(12) United States Patent
Glicksman

(10) Patent No.: US 8,192,486 B2
(45) Date of Patent: Jun. 5, 2012

(54) HUMAN IMPLANTABLE TISSUE EXPANDER

(75) Inventor: Ami Glicksman, Petach Tikva (IL)

(73) Assignee: Implite Ltd., Petach Tikva (IL)

( * ) Notice: Subject to any disclaimer, the term of this patent is extended or adjusted under 35 U.S.C. 154(b) by 463 days.

(21) Appl. No.: 11/918,861

(22) PCT Filed: Jun. 19, 2006

(86) PCT No.: PCT/IL2006/000707
§ 371 (c)(1),
(2), (4) Date: Dec. 4, 2008

(87) PCT Pub. No.: WO2007/000756
PCT Pub. Date: Jan. 4, 2007

(65) Prior Publication Data
US 2009/0093878 A1 Apr. 9, 2009

Related U.S. Application Data

(60) Provisional application No. 60/695,028, filed on Jun. 28, 2005.

(51) Int. Cl.
*A61F 2/12* (2006.01)
(52) U.S. Cl. .......................................................... 623/8
(58) Field of Classification Search ................. 623/7, 8, 623/23.74, 23.67; 606/191–174, 198
See application file for complete search history.

(56) References Cited

U.S. PATENT DOCUMENTS

| | | | |
|---|---|---|---|
| 4,651,717 A | 3/1987 | Jakubczak | |
| 5,358,521 A | 10/1994 | Shane | |
| 5,496,367 A | 3/1996 | Fisher | |
| 5,545,217 A * | 8/1996 | Offray et al. | 623/8 |
| 5,824,081 A | 10/1998 | Knapp et al. | |
| 6,214,045 B1 | 4/2001 | Corbitt, Jr. et al. | |
| 6,228,116 B1 * | 5/2001 | Ledergerber | 623/8 |
| 6,315,796 B1 | 11/2001 | Eaton | |
| 6,432,138 B1 * | 8/2002 | Offray et al. | 623/8 |
| 6,605,116 B2 | 8/2003 | Falcon | |
| 6,802,861 B1 * | 10/2004 | Hamas | 623/7 |
| 2001/0010024 A1 | 7/2001 | Ledergerber | |
| 2003/0074084 A1 | 4/2003 | Nakao | |
| 2004/0148024 A1 | 7/2004 | Williams | |

FOREIGN PATENT DOCUMENTS

| | | |
|---|---|---|
| FR | 2859098 | 8/2003 |
| FR | 2862523 | 11/2003 |

OTHER PUBLICATIONS

Russian Office Action for related U.S. Appl. No. 60/695,028 with partial English translation dated Dec. 14, 2009.
U.S. Appl. No. 60/695,028.
U.S. Appl. No. 60/878,564.

* cited by examiner

*Primary Examiner* — Kevin T Truong
(74) *Attorney, Agent, or Firm* — Husch Blackwell LLP

(57) ABSTRACT

A human implantable tissue expander including a biocompatible implantable structural skeleton element having a predetermined overall three-dimensional shape and defining at least one wall portion having formed therein apertures extending from an interior thereof to an exterior thereof and being operative, when implanted in human tissue, to permit fluid flow through the apertures and to generally maintain the predetermined three-dimensional shape generally independently of its orientation relative to gravitational acceleration.

13 Claims, 23 Drawing Sheets

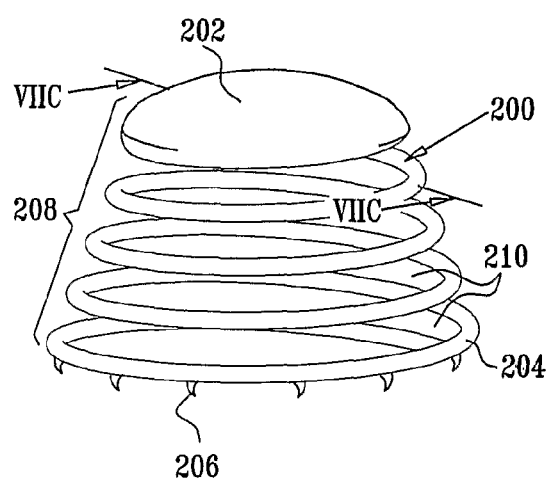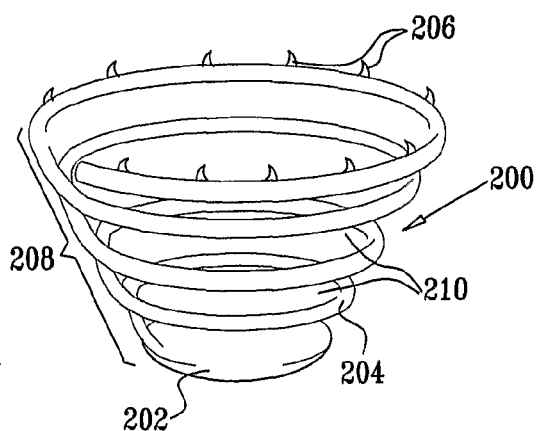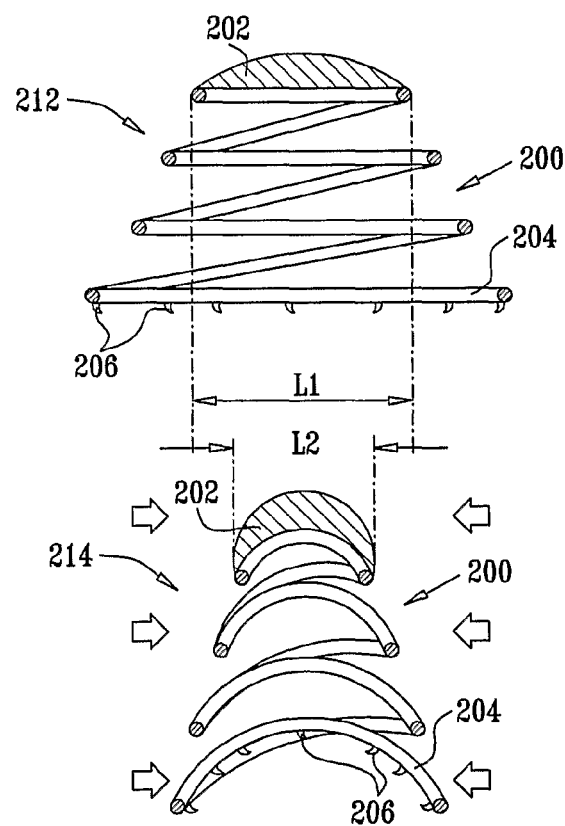

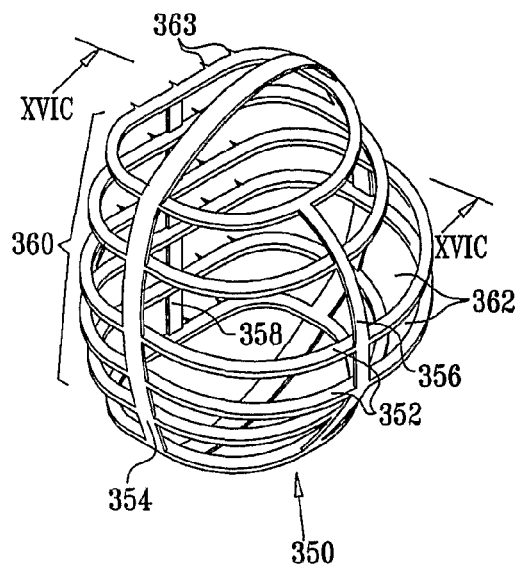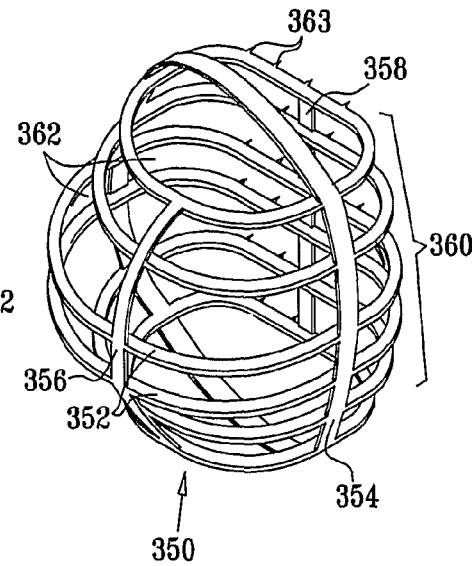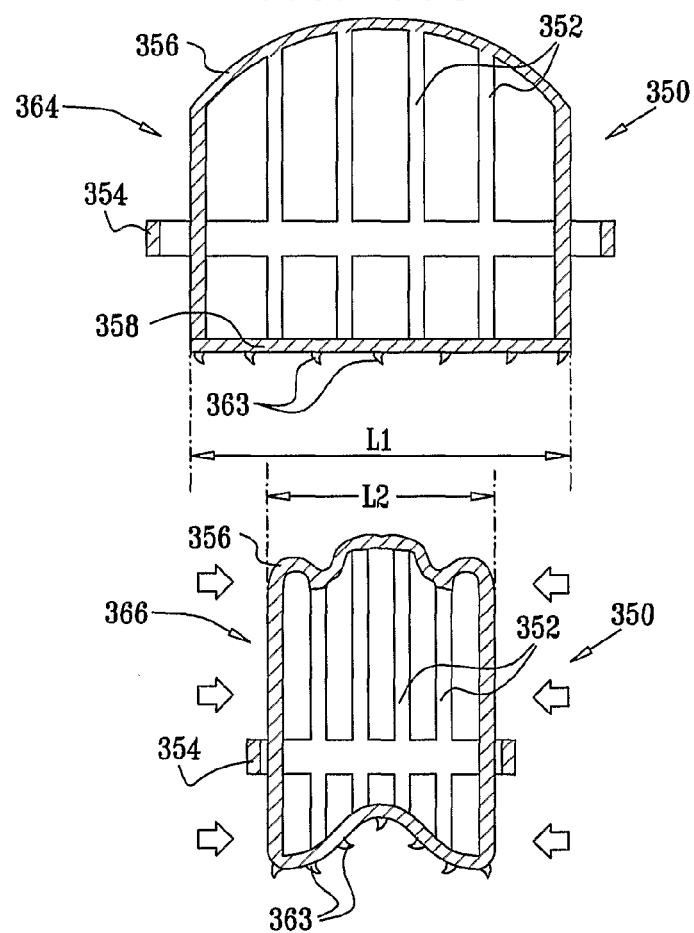

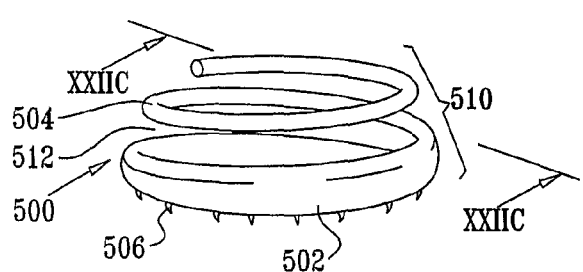
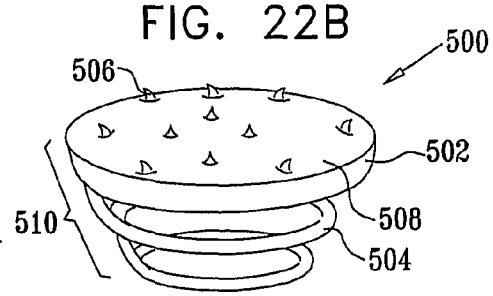
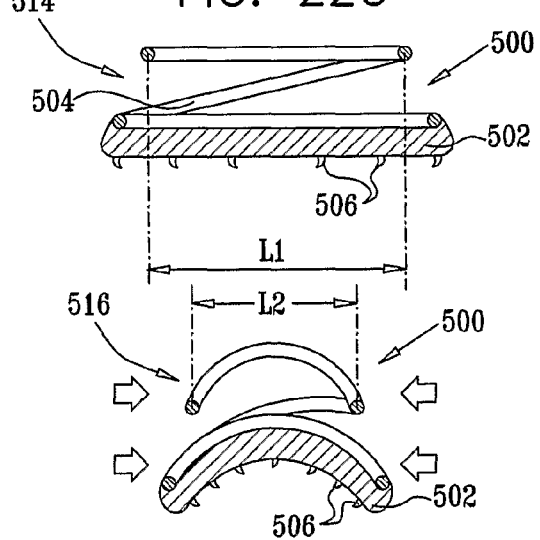

HUMAN IMPLANTABLE TISSUE EXPANDER

REFERENCE TO RELATED APPLICATIONS

This application is a United States National Phase Application based on PCT/IL2006/000707, filed Jun. 19, 2006.

Reference is made to U.S. Provisional Patent Application No. 60/695,028, entitled HUMAN IMPLANTABLE TISSUE EXPANDER, filed Jun. 28, 2005, the disclosure of which is hereby incorporated by reference and priority of which is hereby claimed pursuant to 37 CFR 1.78(a) (4) and (5)(i).

FIELD OF THE INVENTION

The present invention relates to implantable tissue expanders.

BACKGROUND OF THE INVENTION

The following published patent documents are believed to represent the current state of the art:
U.S. Pat. Nos. 6,315,796 and 6,605,116;
French Patent Nos. 2,859,098 and 2,862,523; and
U.S. Patent Application Publication Nos. 2001/0010024; 2003/0074084 and 2004/0148024.

SUMMARY OF THE INVENTION

The present invention seeks to provide improved implantable tissue expanders.

There is thus provided in accordance with a preferred embodiment of the present invention a human implantable tissue expander including a biocompatible implantable structural skeleton element having a predetermined overall three-dimensional shape and defining at least one wall portion having formed therein apertures extending from an interior thereof to an exterior thereof and being operative, when implanted in human tissue, to permit fluid flow through the apertures and to generally maintain the predetermined three-dimensional shape generally independently of its orientation relative to gravitational acceleration.

In accordance with a preferred embodiment of the present invention the human implantable tissue expander also includes at least one cap associated with an exterior of the skeleton element, the skeleton element being operative to maintain the at least one cap in a predetermined three-dimensional configuration generally independently of its orientation relative to gravitational acceleration. Preferably, the skeleton element is integrally formed with the at least one cap. Alternatively or additionally, the skeleton element and the cap are formed of the same material.

In accordance with another preferred embodiment of the present invention the skeleton element includes a plurality of ribs. Preferably, the skeleton element is operative when implanted in human tissue, to maintain a predetermined non-circularly symmetric three-dimensional configuration generally independently of its orientation relative to gravitational acceleration. Additionally or alternatively, the skeleton element is formed of one of polyurethane and silicone. Preferably, the skeleton element is formed by injection molding. Additionally or alternatively, the skeleton element is resilient.

In accordance with yet another preferred embodiment of the present invention the skeleton element is resiliently deformable to a deformed shape in which it has a substantially reduced minimum dimension, thereby to permit insertion of the skeleton element through an aperture in a cutaneous layer when the skeleton element is in the deformed shape and to allow the skeleton element, by virtue of its resiliency, to regain a desired original shape when placed at a desired location within the body.

There is also provided in accordance with another preferred embodiment of the present invention a human implantable tissue expander including a flexible enclosure for at least one material having at least one fluid flow characteristic and a flexible and resilient skeleton associated with the flexible enclosure and being operative to maintain the flexible enclosure in a predetermined three-dimensional configuration generally independently of its orientation relative to gravitational acceleration.

In accordance with a preferred embodiment of the present invention the flexible and resilient skeleton is integrally formed with the flexible enclosure. Preferably, the flexible and resilient skeleton and the flexible enclosure are formed of the same material.

In accordance with another preferred embodiment of the present invention the flexible and resilient skeleton includes a plurality of ribs. Preferably; the flexible and resilient skeleton is formed of one of polyurethane and silicone. Additionally or alternatively, the flexible and resilient skeleton is formed by injection molding.

In accordance with still another preferred embodiment of the present invention the flexible enclosure and the flexible and resilient skeleton are resiliently deformable to a deformed shape in which they have a substantially reduced overall minimum dimension, thereby to permit insertion of the flexible enclosure and the flexible and resilient skeleton through an aperture in a cutaneous layer when the flexible enclosure and the flexible and resilient skeleton are in the deformed shape and to allow the flexible enclosure and the flexible and resilient skeleton, by virtue of resiliency of the flexible and resilient skeleton, to regain a desired original shape when placed at a desired location within the body.

In accordance with yet another preferred embodiment of the present invention the at least one material is a gas. Alternatively, the at least one material is a liquid. As a further alternative, the at least one material is formed of particles.

In accordance with a further preferred embodiment of the present invention the flexible enclosure includes an injection port. Preferably, the flexible enclosure contains the at least one material. Additionally or alternatively, the flexible enclosure does not contain the at least one material when the flexible enclosure is inserted through the aperture.

BRIEF DESCRIPTION OF THE DRAWINGS

The present invention will be understood and appreciated more fully from the following detailed description, taken in conjunction with the drawings in which:

FIGS. 7A and 7B are simplified respective top and bottom pictorial view illustrations of an implantable breast tissue expander constructed and operative in accordance with a further preferred embodiment of the present invention;

FIG. 7C is a simplified illustration showing deformation of the implantable breast tissue expander of FIGS. 7A and 7B to reduce the minimum dimension thereof;

FIGS. 5A and 8B are simplified respective pictorial and sectional illustrations of the implantable breast tissue expander of FIGS. 7A and 7B, implanted in a patient positioned in a standing orientation;

FIGS. 16A and 16B are simplified respective top and bottom pictorial view illustrations of an implantable breast tissue expander constructed and operative in accordance with still another preferred embodiment of the present invention;

FIG. 16C is a simplified illustration showing deformation of the implantable breast tissue expander of FIGS. 16A and 16B to reduce the minimum dimension thereof;

FIGS. 22A and 22B are simplified respective top and bottom pictorial view illustrations of an implantable tissue expander constructed and operative in accordance with a further preferred embodiment of the present invention;

FIG. 22C is a simplified illustration showing deformation of the implantable tissue expander of FIGS. 22A and 22B to reduce the minimum dimension thereof.

DETAILED DESCRIPTION OF PREFERRED EMBODIMENTS

Reference is now made to FIGS. 1A-3B, which illustrate a breast tissue expander constructed and operative in accordance with a preferred embodiment of the present invention. The breast tissue expander of FIGS. 1A-3B is generally characterized in that it comprises a biocompatible, preferably resilient, implantable structural skeleton element 100 having a predetermined overall three-dimensional shape, defining at least one wall portion having formed therein apertures extending from an interior thereof to an exterior thereof and being operative, when implanted in human tissue, to generally maintain the predetermined three-dimensional shape generally independently of its orientation relative to gravitational acceleration.

The term "skeleton element" is used throughout to refer to an element which itself provides structural support and defines a predetermined three-dimensional shape, irrespective of whether and to what extent it is inflated or otherwise filled with a fluid or other material. It may thus be appreciated that a skeleton element is distinguished from prior art prostheses which comprise a flexible bag which is filled with a fluid or gel and whose three-dimensional shape is governed by the extent to which it is filled or is readily changeable in response to its orientation.

The skeleton element of the present invention may be incorporated in or associated with a fluid-filled enclosure to define a tissue expander. In such a case, the overall shape of the tissue expander is determined generally by the shape of the skeleton element rather than by the enclosure, the extent of its filling or its internal pressurization.

Figure 1A:
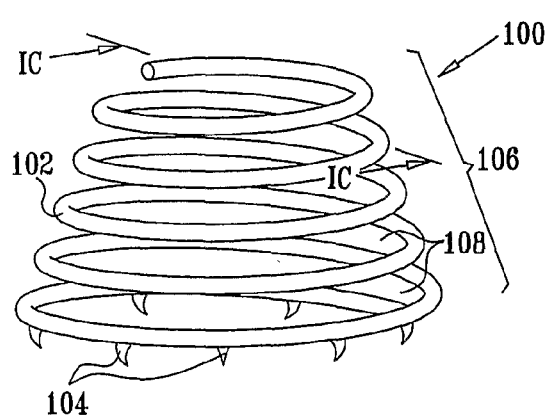
FIGS. 1A and 1B are simplified respective top and bottom pictorial view illustrations of an implantable breast tissue expander constructed and operative in accordance with a preferred embodiment of the present invention.
Figure 1B:
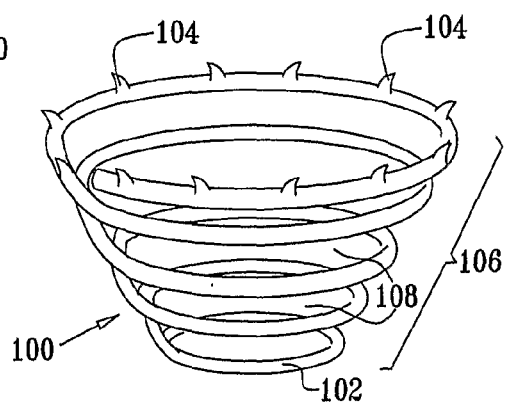

As seen in FIGS. 1A and 1B, the skeleton element 100 is typically in the shape of a truncated, generally conically-shaped coiled elongate element 102 having variously directed positioning barbs 104 located at base locations therealong. Elongate element 102 is preferably formed of a biocompatible plastic material, such as polyurethane or silicone. A suitable stiffener, such as a metal wire, may be incorporated in the elongate element 102. Elongate element 102 preferably defines at least one wall portion 106 having formed therein apertures 108, extending from an interior thereof to an exterior thereof, which are operative, when the breast tissue expander is implanted, to permit fluid flow therethrough.

Figure 1C:
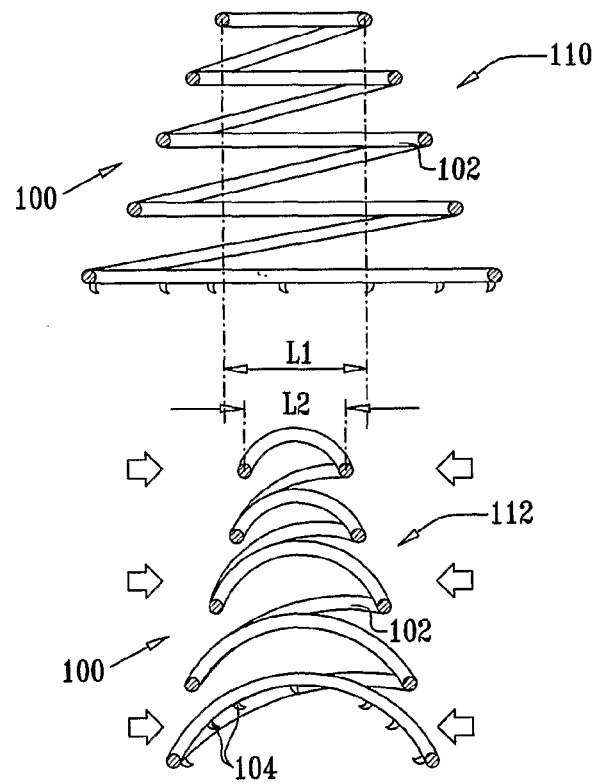
FIG. 1C is a simplified illustration showing deformation of the implantable breast tissue expander of FIGS. 1A and 1B to reduce the minimum dimension thereof.

As illustrated in FIG. 1C, it is a particular feature of a preferred embodiment of the present invention that skeleton element 100 is resiliently deformable from its normal shape, as shown in FIGS. 1A and 1B and designated generally in FIG. 1C by reference numeral 110, having a minimum dimension L1, to a deformed shape, designated generally by reference numeral 112, in which it has a substantially reduced minimum dimension L2, thereby to permit insertion of the skeleton element 100, in its deformed shape 112, through an aperture (not shown) in a cutaneous layer (not shown) and to allow the skeleton element 100, by virtue of its resiliency, to regain its normal shape 110 when placed at a desired location within the body (not shown).

Figure 2A:
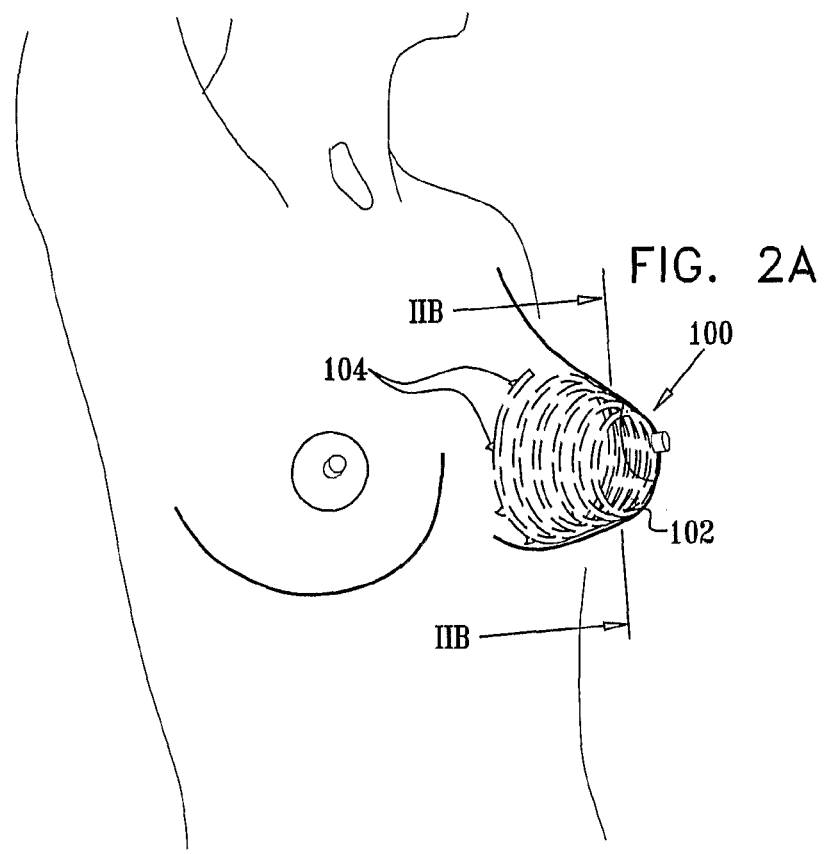
FIGS. 2A and 2B are respective pictorial and sectional illustrations of the implantable breast tissue expander of FIGS. 1A and 1B, implanted in a patient positioned in a standing orientation.
Figure 2B:
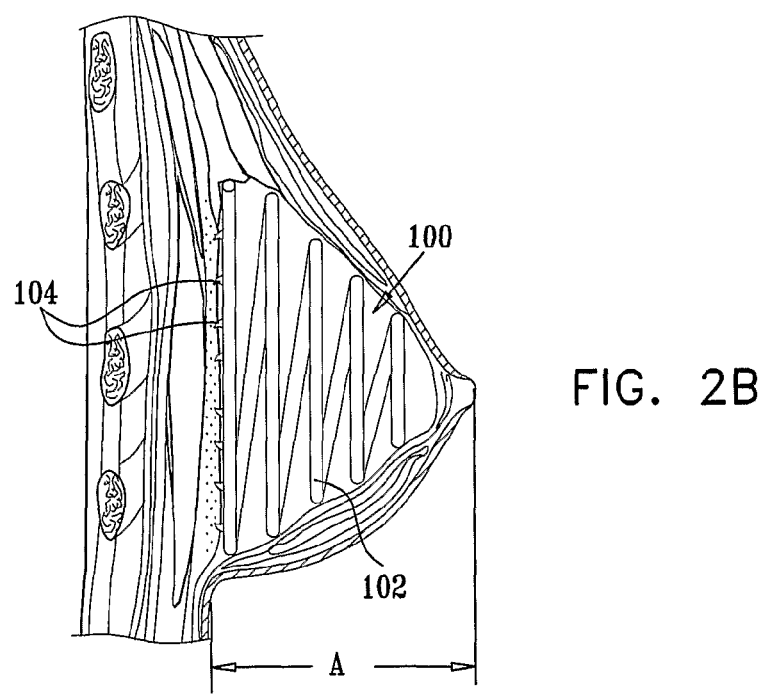
Figure 3A:
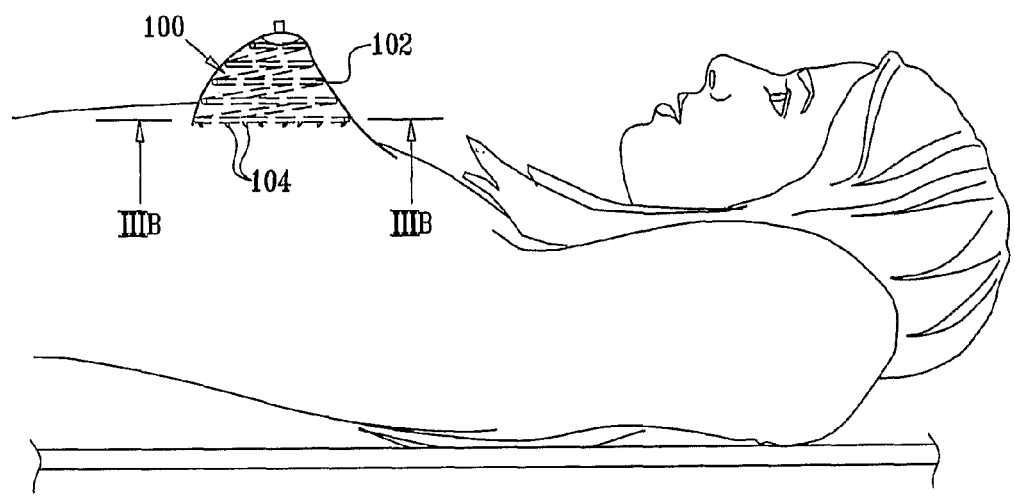
FIGS. 3A and 3B are respective pictorial and sectional illustrations of the implantable breast tissue expander of FIGS. 1A and 1B, implanted in a patient positioned in a prone orientation.
Figure 3B:
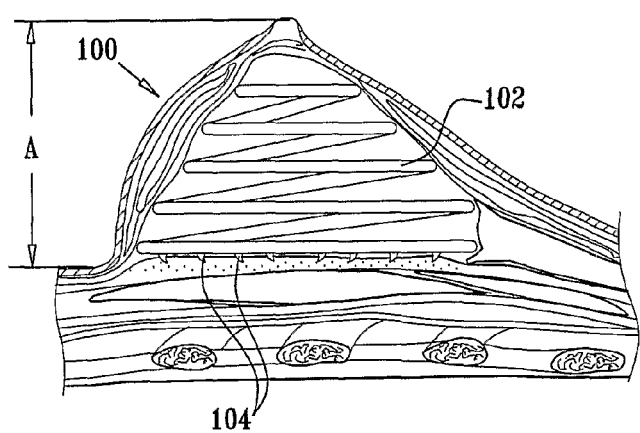

Turning to FIGS. 2A and 2B, which illustrate the tissue expander in the form of skeleton element 100 implanted in a breast, it is seen that the general three-dimensional configuration of the skeleton element 100, as it appears in FIGS. 1A and 1B, is maintained when the skeleton element 100 is implanted. Considering also FIGS. 3A and 3B, it is appreciated that the general three-dimensional configuration of the skeleton element 100, as it appears in FIGS. 1A and 1B, is maintained essentially unchanged irrespective of whether the patient is standing or lying prone, as shown by distance A in FIGS. 2B and 3B.

Reference is now made to FIGS. 4A-6B, which illustrate a breast tissue expander constructed and operative in accordance with another preferred embodiment of the present invention. The breast tissue expander of FIGS. 4A-6B is generally characterized in that it comprises a biocompatible resilient implantable structural skeleton element 150 entirely enclosed in a fluid enclosure 152 having a shape which is generally determined by the predetermined overall three-dimensional shape of the skeleton element 150. The breast tissue expander of FIGS. 4A-6B is operative, when implanted in human tissue, to generally maintain the predetermined three-dimensional shape generally independently of its orientation relative to gravitational acceleration.

Figure 4A:
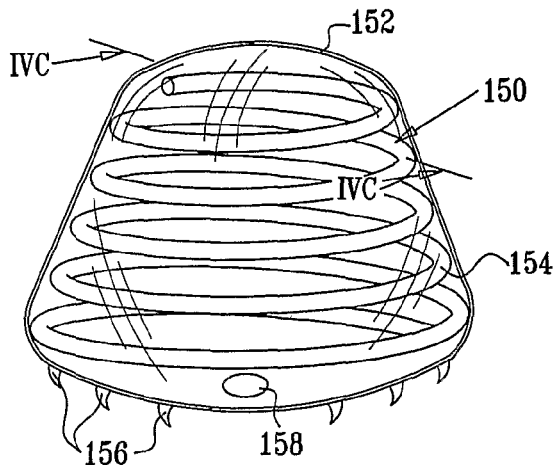
FIGS. 4A and 4B are respective top and bottom pictorial view illustrations of a gas filled implantable breast tissue expander constructed and operative in accordance with another preferred embodiment of the present invention.
Figure 4B:
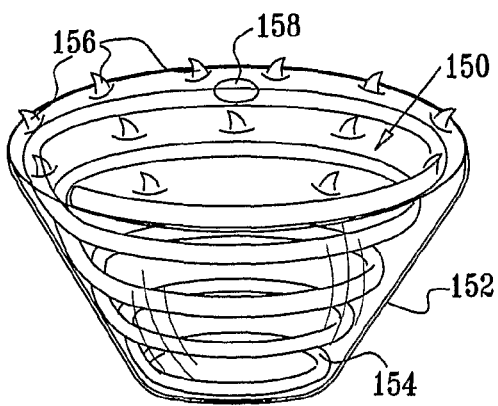

As seen in FIGS. 4A and 4B, the skeleton element 150 is typically in the shape of a truncated, generally conically-shaped coiled elongate element 154 and the fluid enclosure 152 has variously directed positioning barbs 156 located at base locations therealong. Elongate element 154 is preferably formed of a biocompatible plastic material, such as polyurethane or silicone. A suitable stiffener, such as a metal wire, may be incorporated in the elongate element 154. The fluid enclosure 152 is preferably formed of an elastomer, such as silicone, and preferably includes a conventional injection port 158.

Figure 4C:
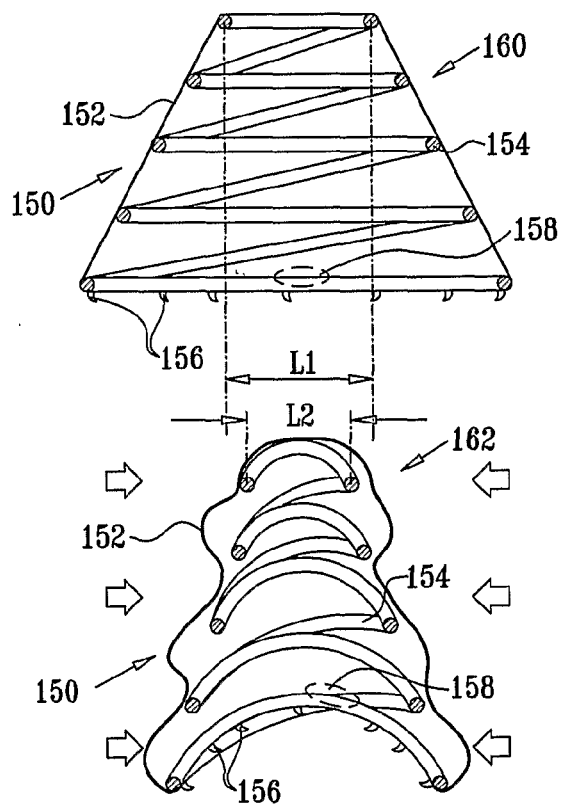
FIG. 4C is a simplified illustration showing deformation of the implantable breast tissue expander of FIGS. 4A and 4B to reduce the minimum dimension thereof.

As illustrated in FIG. 4C, it is a particular feature of a preferred embodiment of the present invention that skeleton element 150 and fluid enclosure 152 are resiliently deformable from their normal shape, as shown in FIGS. 4A and 4B and designated generally in FIG. 4C by reference numeral 160, having a minimum dimension L1, to a deformed shape, designated generally by reference numeral 162, in which they have a substantially reduced minimum dimension L2, thereby to permit insertion of the skeleton element 150 and the fluid enclosure 152, in their deformed shape 162, through an aperture (not shown) in a cutaneous layer (not shown) and to allow the skeleton element 150 and the fluid enclosure 152, by virtue of the resiliency of the skeleton element, to regain their normal shape 160 when placed at a desired location within the body (not shown). It is appreciated that the skeleton element 150 may be separate from the fluid enclosure 152 as illustrated in FIG. 4C. Alternatively, the skeleton element 150 may be wholly or partially joined to the fluid enclosure 152.

Figure 5A:
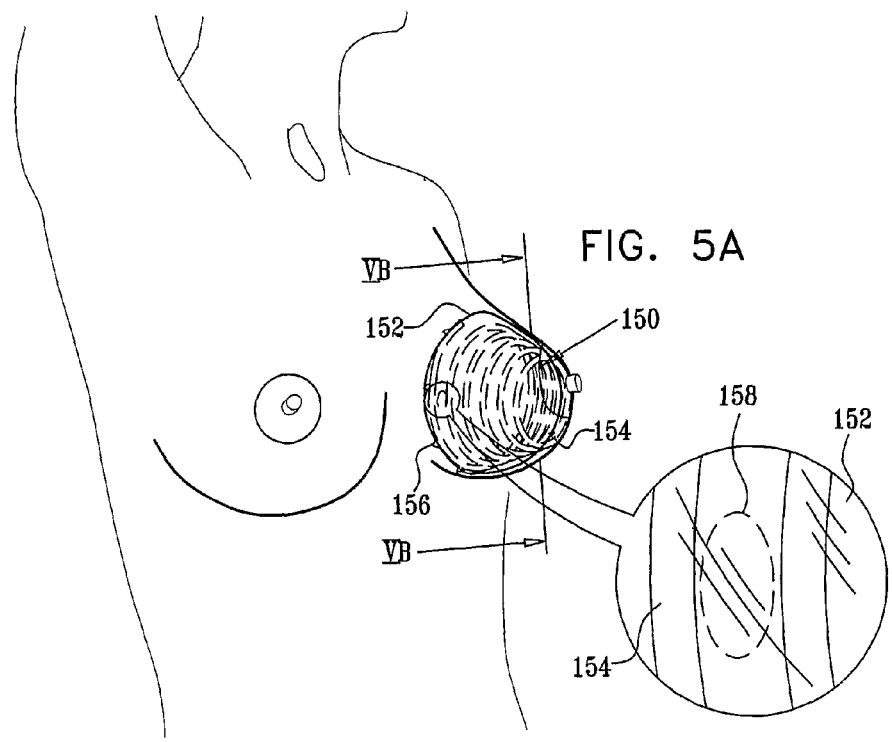
FIGS. 5A and 5B are simplified respective pictorial and sectional illustrations of the implantable breast tissue expander of FIGS. 4A and 4B, implanted in a patient positioned in a standing orientation.
Figure 5B:
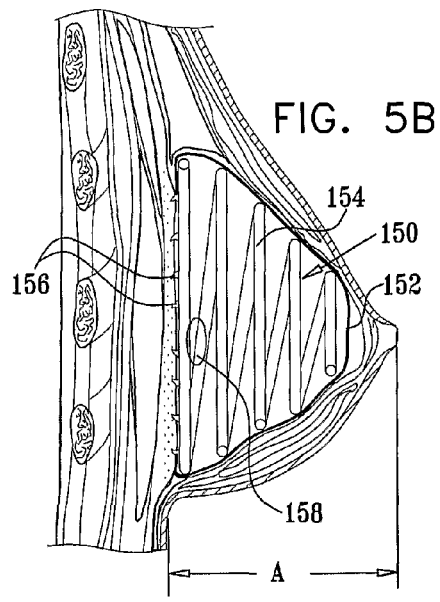

Turning to FIGS. 5A and 5B, which illustrate the tissue expander in the form of skeleton element 150 implanted in a breast, it is seen that the general three-dimensional configuration of the skeleton element 150, as it appears in FIGS. 4A and 4B, is maintained when the tissue expander is implanted. Considering also FIGS. 6A and 6B, it is appreciated that the general three-dimensional configuration of the skeleton element 150, as it appears in FIGS. 4A and 4B, is maintained essentially unchanged irrespective of whether the patient is standing or lying prone, as shown by distance A in FIGS. 5B and 6B.

Figure 5C:
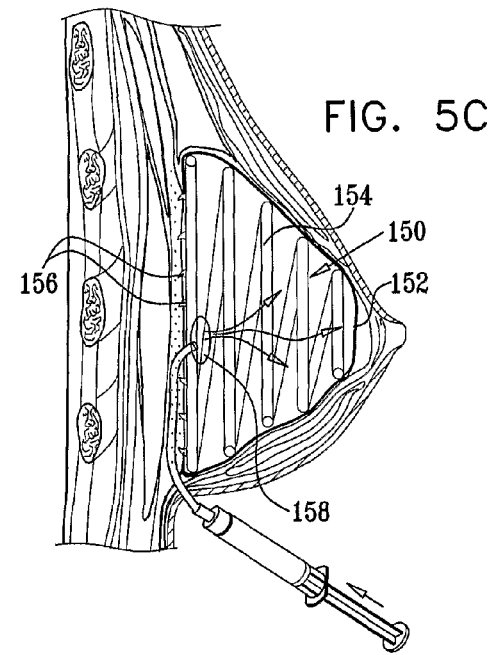
FIG. 5C illustrates addition of fluid to the implantable breast tissue expander of FIGS. 4A-5B, thereby increasing the internal pressure thereof.
Figure 6A:
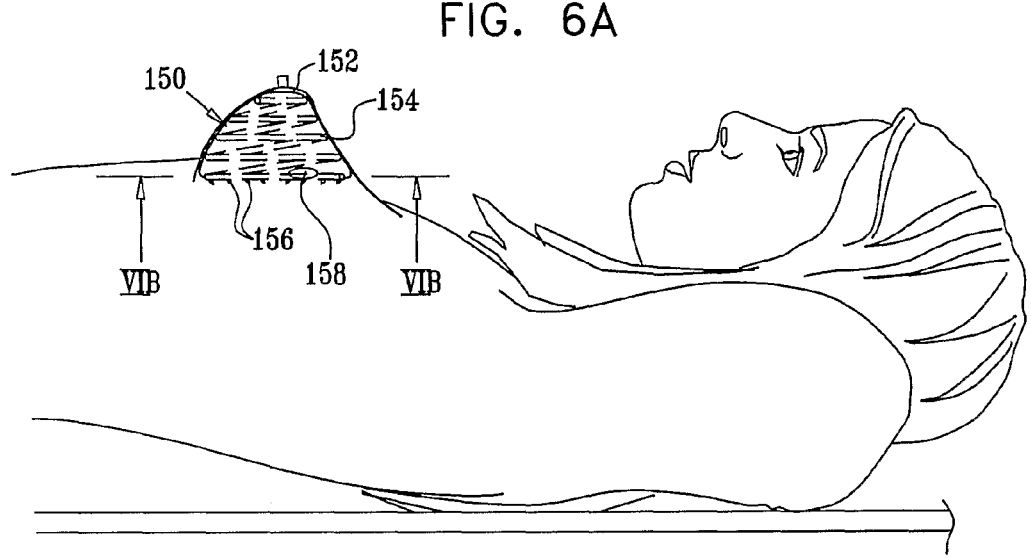
FIGS. 6A and 6B are simplified respective pictorial and sectional illustrations of the implantable breast tissue expander of FIGS. 4A and 4B, implanted in a patient positioned in a prone orientation.
Figure 6B:
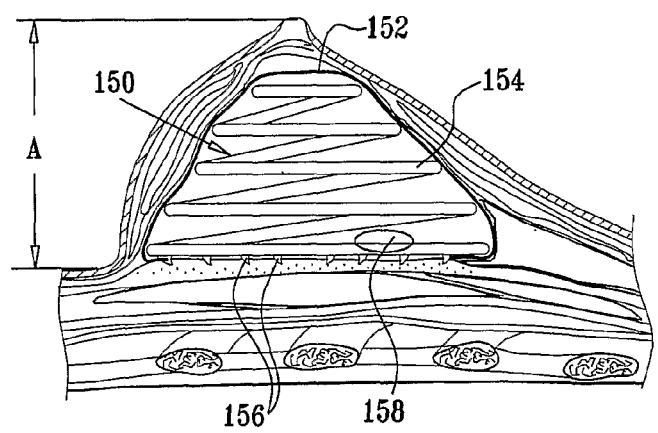

FIG. 5C schematically illustrates changing the pressurization inside fluid enclosure 152, as by injection of a fluid into the interior of the enclosure 152 via injection port 158. Alternatively, a material formed of particles, which are preferably smaller in diameter than the diameter of the injection device, may be used to change the pressurization inside enclosure 152. The change in pressurization may take place at any suitable time prior to or following implantation of the tissue expander.

Reference is now made to FIGS. 7A-9B, which illustrate a breast tissue expander constructed and operative in accordance with a further preferred embodiment of the present invention. The breast tissue expander of FIGS. 7A-9B is generally characterized in that it comprises a biocompatible resilient implantable structural skeleton element 200 having associated therewith a flexible cap 202 having a shape which is generally determined by the predetermined overall three-dimensional shape of the skeleton element 200. The breast tissue expander of FIGS. 7A-9B defines at least one wall portion having formed therein apertures extending from an interior thereof to an exterior thereof is operative, when implanted in human tissue, to generally maintain the predetermined three-dimensional shape generally independently of its orientation relative to gravitational acceleration.

As seen in FIGS. 7A and 7B, the skeleton element 200 is typically in the shape of a truncated, generally conically-shaped coiled elongate element 204 having variously directed positioning barbs 206 located at base locations therealong. Cap 202 and elongate element 204 are preferably formed of biocompatible plastic materials, such as polyurethane or silicone. A suitable stiffener, such as a metal wire, may be incorporated in the elongate element 204. Elongate element 204 preferably defines at least one wall portion 208 having formed therein apertures 210, extending from an interior thereof to an exterior thereof, which are operative, when the breast tissue expander is implanted, to permit fluid flow therethrough.

As illustrated in FIG. 7C, it is a particular feature of a preferred embodiment of the present invention that skeleton element 200 is resiliently deformable from its normal shape, as shown in FIGS. 7A and 7B and designated generally in FIG. 7C by reference numeral 212, having a minimum dimension L1, to a deformed shape, designated generally by reference numeral 214, in which it has a substantially reduced minimum dimension L2, thereby to permit insertion of the skeleton element 200, in its deformed shape 214, through an aperture (not shown) in a cutaneous layer (not shown) and to allow the skeleton element 200, by virtue of its resiliency, to regain its normal shape 212 when placed at a desired location within the body (not shown).

Figure 8A:
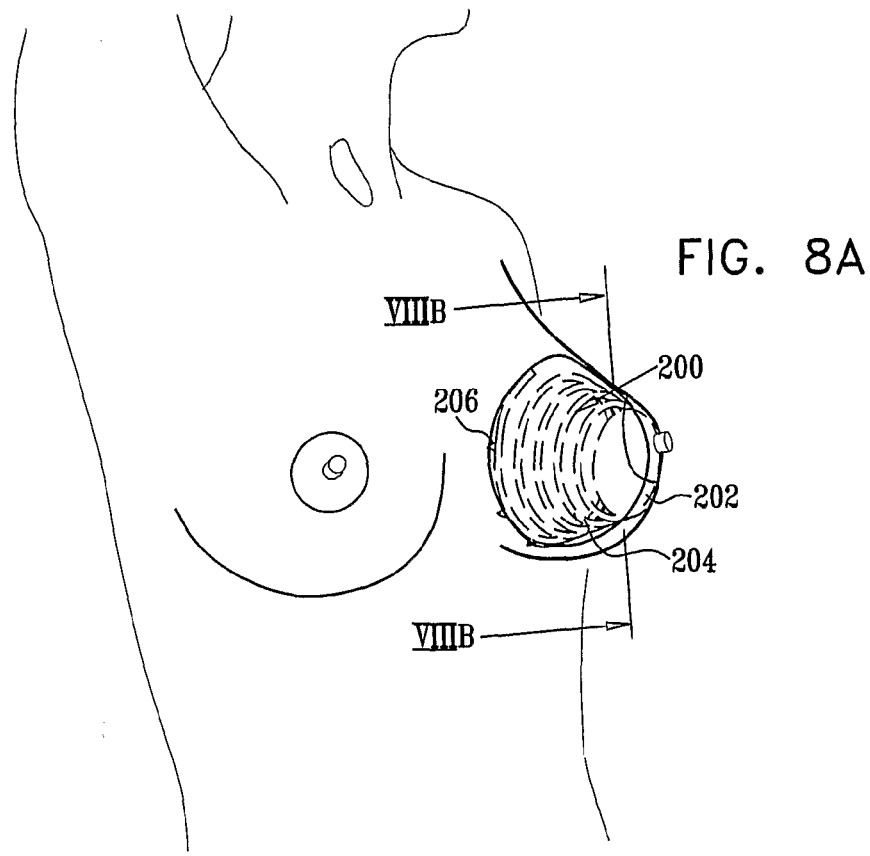
Figure 8B:
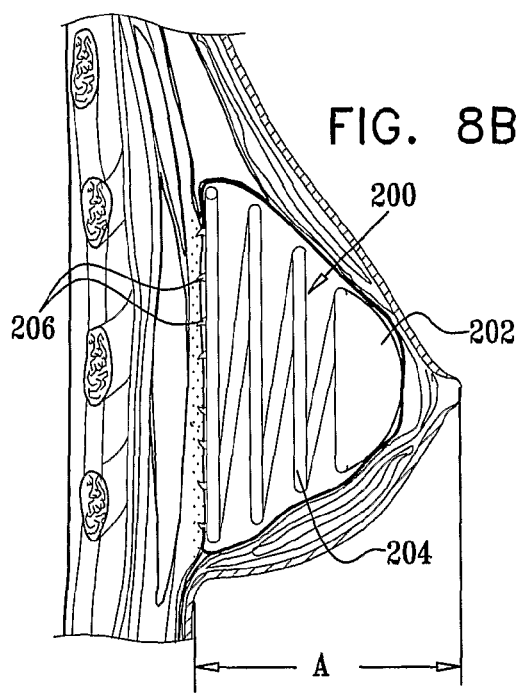
Figure 9A:
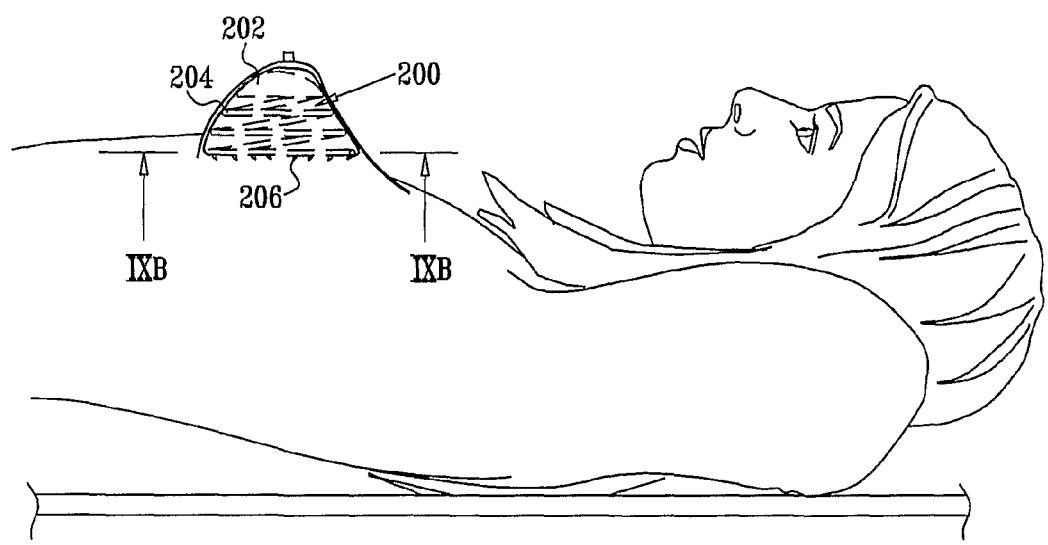
FIGS. 9A and 9B are simplified respective pictorial and sectional illustrations of the implantable breast tissue expander of FIGS. 7A and 7B, implanted in a patient positioned in a prone orientation.
Figure 9B:
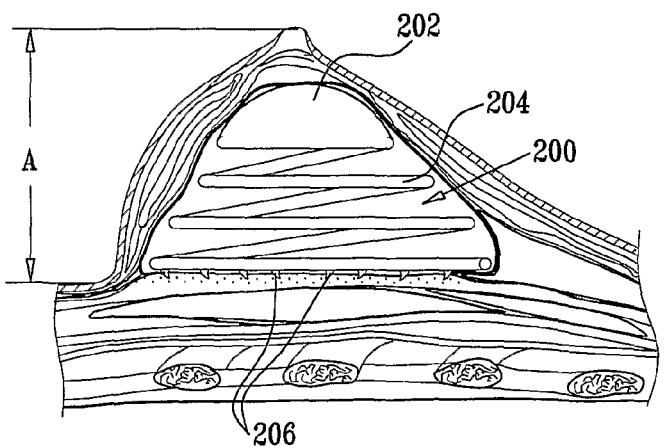

Turning to FIGS. 8A and 8B, which illustrate the tissue expander in the form of skeleton element 200 implanted in a breast, it is seen that the general three-dimensional configuration of the skeleton element 200, as it appears in FIGS. 7A and 7B, is maintained when the tissue expander is implanted. Considering also FIGS. 9A and 9B, it is appreciated that the general three-dimensional configuration of the skeleton element 200, as it appears in FIGS. 7A and 7B, is maintained essentially unchanged irrespective of whether the patient is standing or lying prone, as shown by distance A in FIGS. 8B and 9B.

Reference is now made to FIGS. 10A-12B, which illustrate a breast tissue expander constructed and operative in accordance with yet another preferred embodiment of the present invention. The breast tissue expander of FIGS. 10A-12B is generally characterized in that it comprises a biocompatible resilient implantable structural skeleton element 250 having a predetermined overall three-dimensional shape and being operative, when implanted in human tissue, to generally maintain the predetermined three-dimensional shape generally independently of its orientation relative to gravitational acceleration.

Figure 10A:
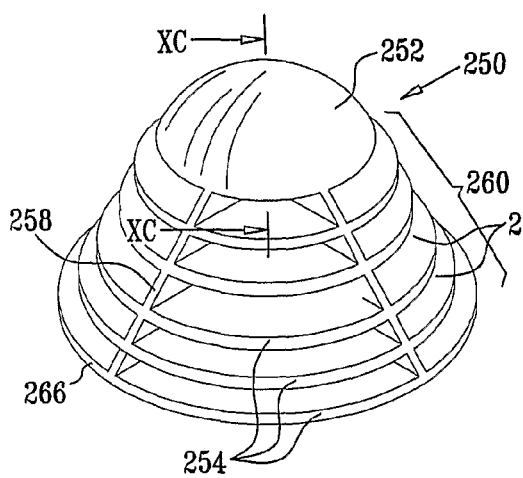
FIGS. 10A and 10B are simplified respective top and bottom pictorial view illustrations of an implantable breast tissue expander constructed and operative in accordance with yet another preferred embodiment of the present invention.
Figure 10B:
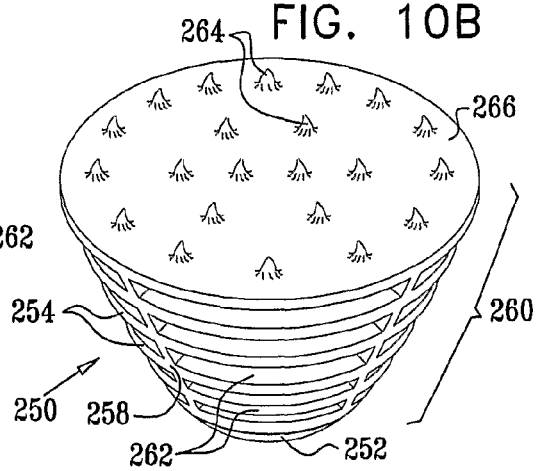

As seen in FIGS. 10A and 10B, the skeleton element 250 has a generally conical shape having a generally hemispherical vertex 252. Skeleton element 250 includes a plurality of generally circular discs 254 extending radially outward from a core 256 (FIGS. 11B and 12B) and additionally supported by ribs 258, defining at least one wall portion having formed therein apertures extending from an interior thereof to an exterior thereof, which are operative, when the breast tissue expander is implanted, to permit fluid flow therethrough.

Skeleton element 250 preferably defines at least one wall portion 260 having formed therein apertures 262, extending from an interior thereof to an exterior thereof, Variously directed positioning barbs 264 are located on a base disc 266 located at base locations therealong. Skeleton element 250 is preferably formed of a biocompatible plastic material as polyurethane or silicone.

Figure 10C:
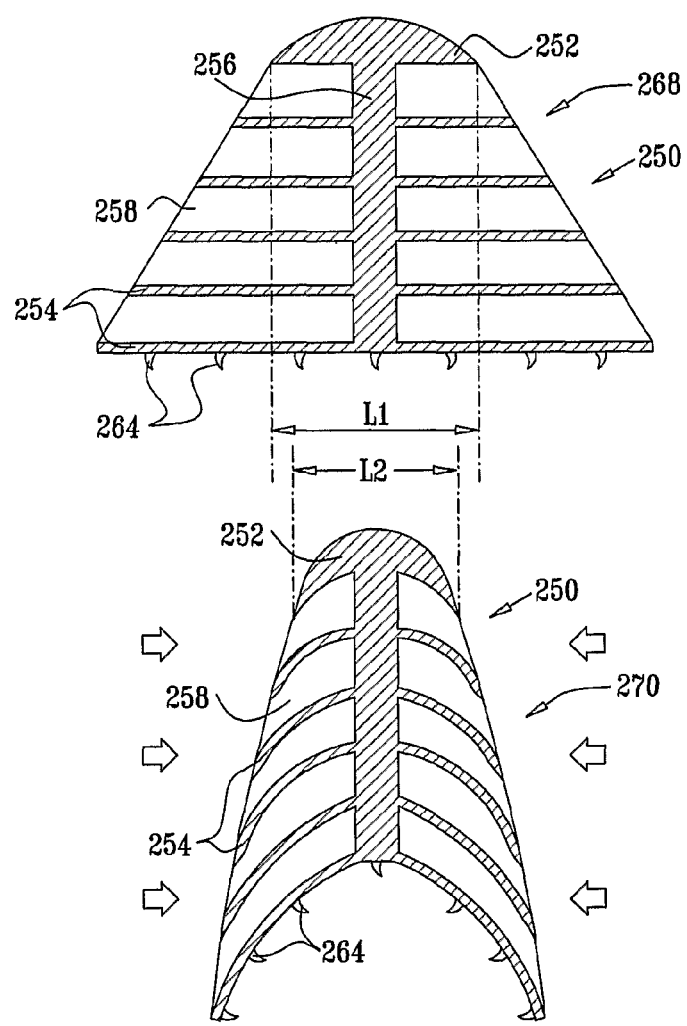
FIG. 10C is a simplified illustration showing deformation of the implantable breast tissue expander of FIGS. 10A and 10B to reduce the minimum dimension thereof.

As illustrated in FIG. 10C, it is a particular feature of a preferred embodiment of the present invention that skeleton element 250 is resiliently deformable from its normal shape, as shown in FIGS. 10A and 10B and designated generally in FIG. 10C by reference numeral 268, having a minimum dimension L1, to a deformed shape, designated generally by reference numeral 270, in which it has a substantially reduced minimum dimension L2, thereby to permit insertion of the skeleton element 250, in its deformed shape 270, through an aperture (not shown) in a cutaneous layer (not shown) and to allow the skeleton element 250, by virtue of its resiliency, to regain its normal shape 268 when placed at a desired location within the body (not shown).

Figure 11A:
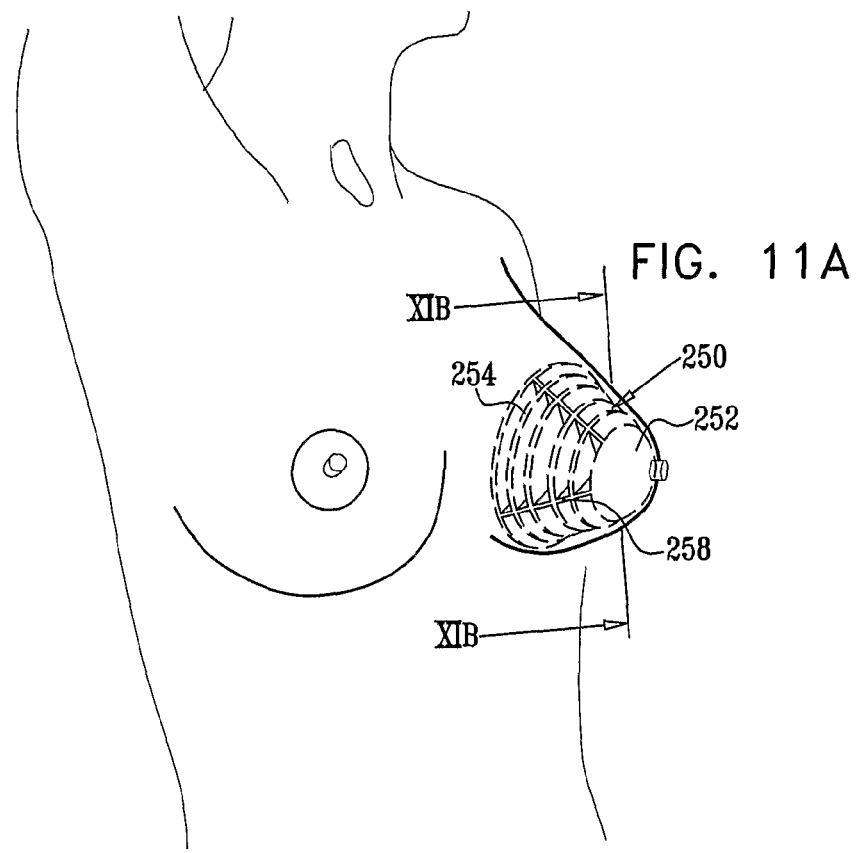
FIGS. 11A and 11B are simplified respective pictorial and sectional illustrations of the implantable breast tissue expander of FIGS. 10A and 10B, implanted in a patient positioned in a standing orientation.
Figure 11B:
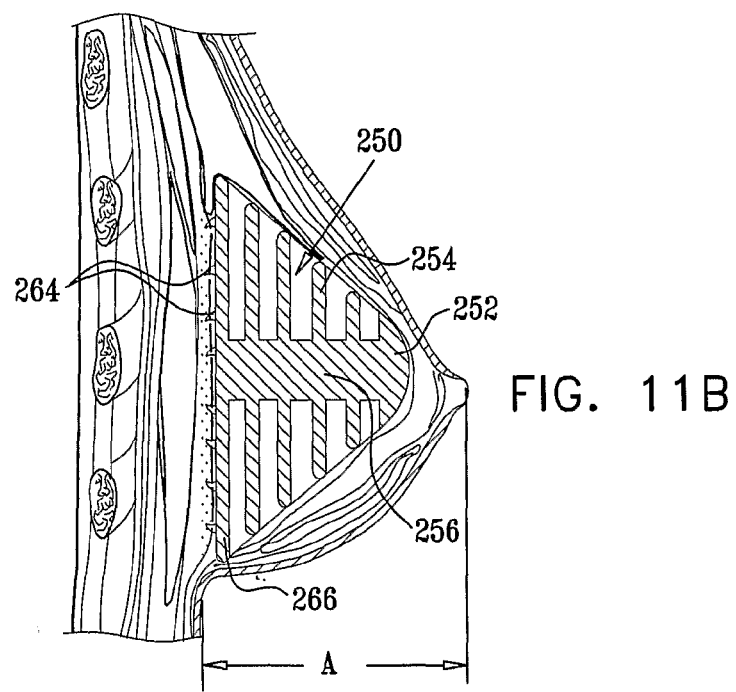
Figure 12A:
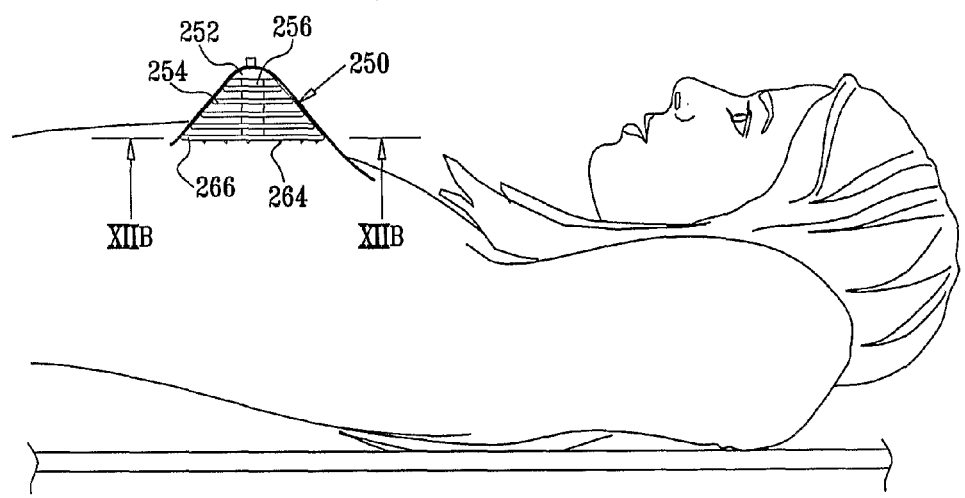
FIGS. 12A and 12B are simplified respective pictorial and sectional illustrations of the implantable breast tissue expander of FIGS. 10A and 10B, implanted in a patient positioned in a prone orientation.
Figure 12B:
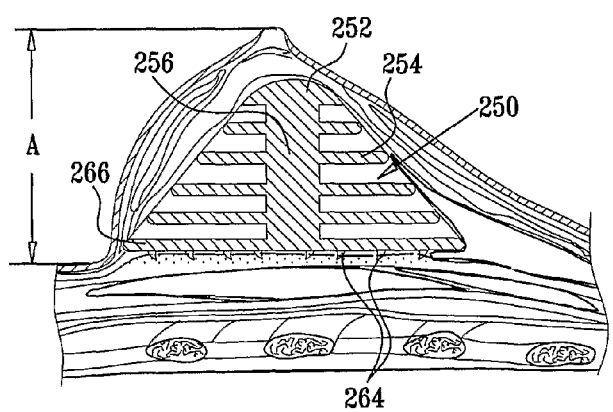

Turning to FIGS. 11A and 11B, which illustrate the tissue expander in the form of skeleton element 250 implanted in a breast, it is seen that the general three-dimensional configuration of the skeleton element 250, as it appears in FIGS. 10A and 10B, is maintained when the skeleton element 250 is implanted. Considering also FIGS. 12A and 12B, it is appreciated that the general three-dimensional configuration of the skeleton element 250, as it appears in FIGS. 10A and 10B, is maintained essentially unchanged irrespective of whether the patient is standing or lying prone, as shown by distance A in FIGS. 11B and 12B.

Reference is now made to FIGS. 13A-15B, which illustrate a breast tissue expander constructed and operative in accordance with still another preferred embodiment of the present invention. The breast tissue expander of FIGS. 13A-15B is generally characterized in that it comprises a biocompatible resilient implantable structural skeleton element 300 entirely enclosed in a fluid enclosure 302 having a shape which is generally determined by the predetermined overall three-dimensional shape of the skeleton element 300. The breast tissue expander of FIGS. 13A-15B is operative, when implanted in human tissue, to generally maintain the predetermined three-dimensional shape generally independently of its orientation relative to gravitational acceleration.

Figure 13A:
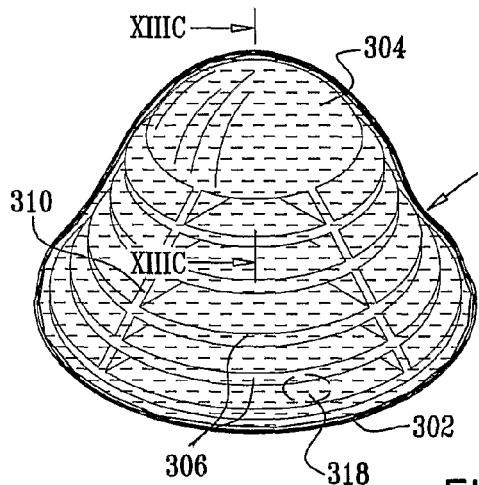
FIGS. 13A and 13B are simplified respective top and bottom pictorial view illustrations of a fluid-filled implantable breast tissue expander constructed and operative in accordance with yet another preferred embodiment of the present invention.
Figure 13B:
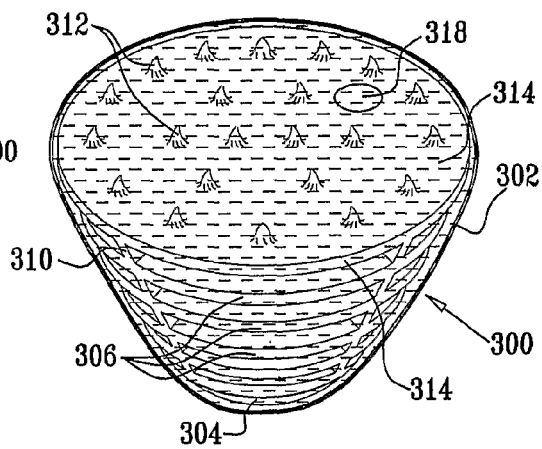

As seen in FIGS. 13A and 13B, the skeleton element 300 has a generally conical shape having a generally hemispherical vertex 304. Skeleton element 300 is formed of a plurality of generally circular discs 306 extending radially outward from a core 308 (FIGS. 14B and 15B) and additionally supported by ribs 310. Variously directed positioning barbs 312 are located on a base disc 314 located at base locations therealong. Skeleton element 300 is preferably formed of a biocompatible plastic material, such as polyurethane or silicone. The fluid enclosure 302 is preferably formed of an elastomer, such as silicone, and preferably includes a conventional injection port 318.

Figure 13C:
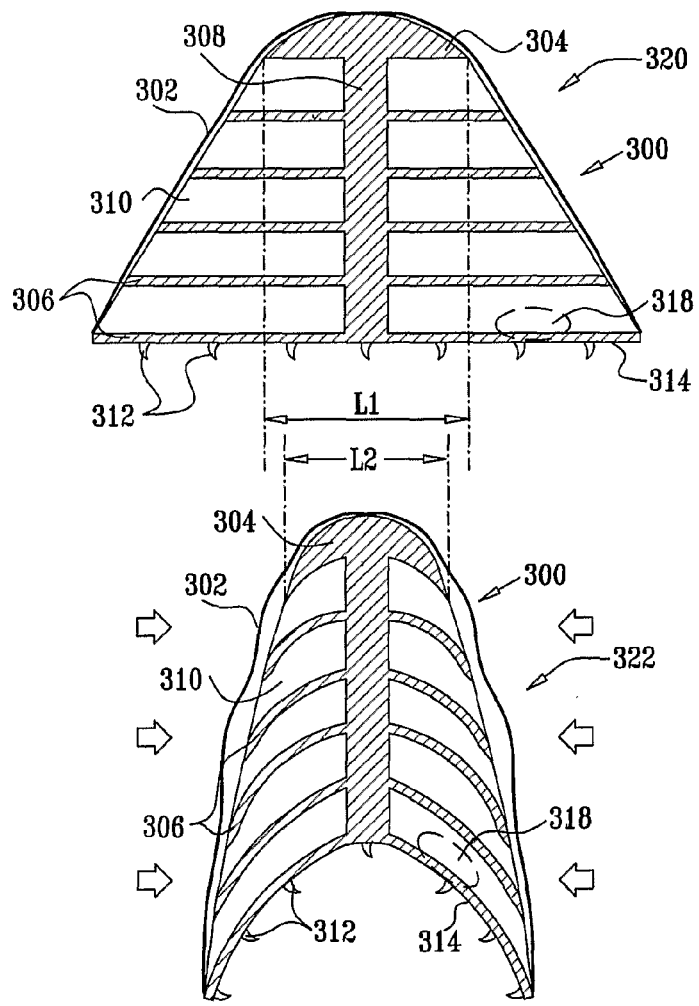
FIG. 13C is a simplified illustration showing deformation of the implantable breast tissue expander of FIGS. 13A and 13B to reduce the minimum dimension thereof.

As illustrated in FIG. 13C, it is a particular feature of a preferred embodiment of the present invention that skeleton element 300 and fluid enclosure 302 are resiliently deformable from their normal shape, as shown in FIGS. 13A and 13B and designated generally in FIG. 13C by reference numeral 320, having a minimum dimension L1, to a deformed shape, designated generally by reference numeral 322, in which they have a substantially reduced minimum dimension L2, thereby to permit insertion of the skeleton element 300 and the fluid enclosure 302, in their deformed shape 322, through an aperture (not shown) in a cutaneous layer (not shown) and to allow the skeleton element 300 and the fluid enclosure 302, by virtue of the resiliency of the skeleton element, to regain their normal shape 320 when placed at a desired location within the body (not shown). It is appreciated that the skeleton element 300 may be separate from the fluid enclosure 302 as illustrated in FIG. 13C. Alternatively, the skeleton element 300 may be wholly or partially joined to the fluid enclosure 302.

Figure 14A:
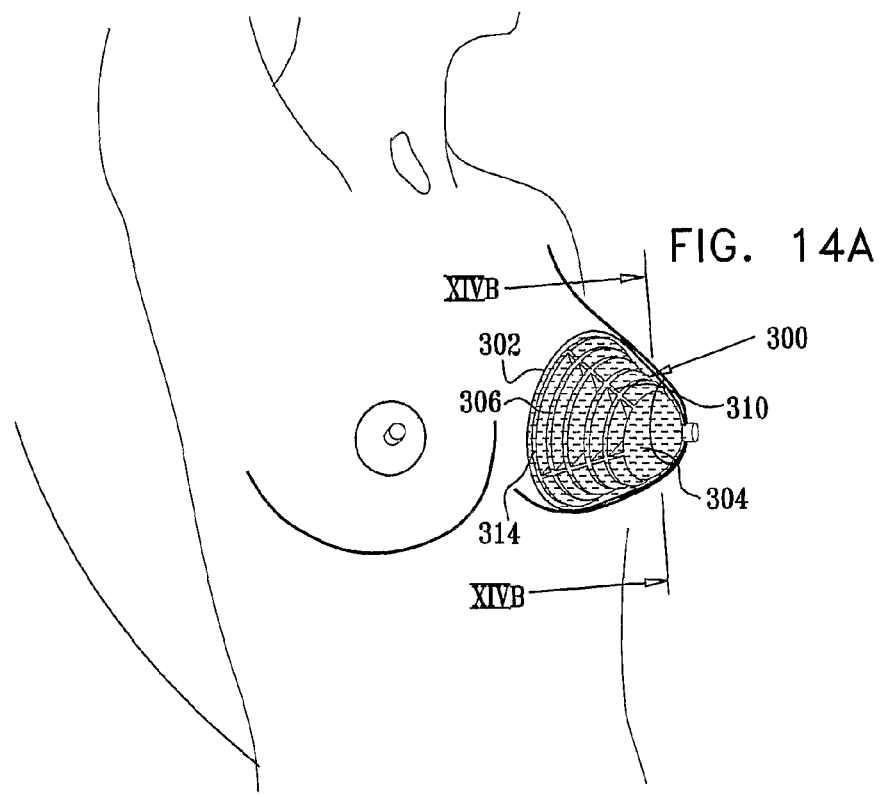
FIGS. 14A and 14B are simplified respective pictorial and sectional illustrations of the implantable breast tissue expander of FIGS. 13A and 13B, implanted in a patient positioned in a standing orientation.
Figure 14B:
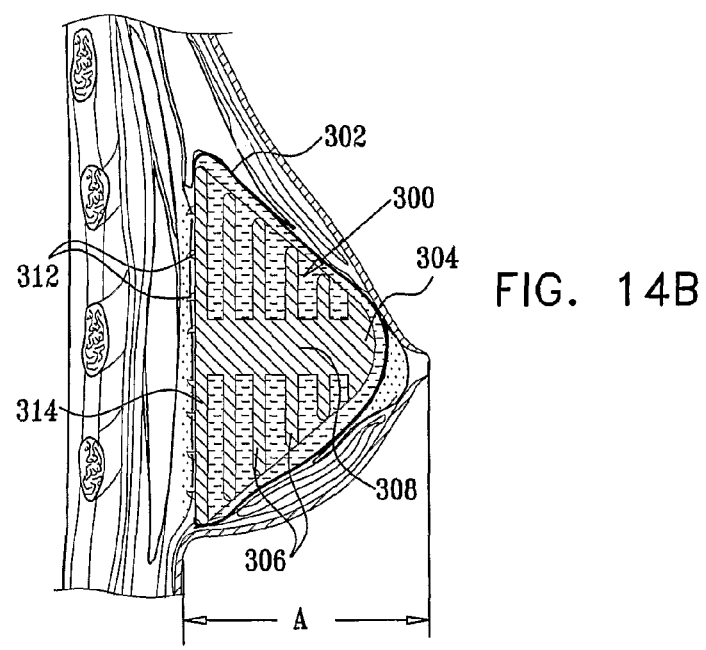
Figure 15A:
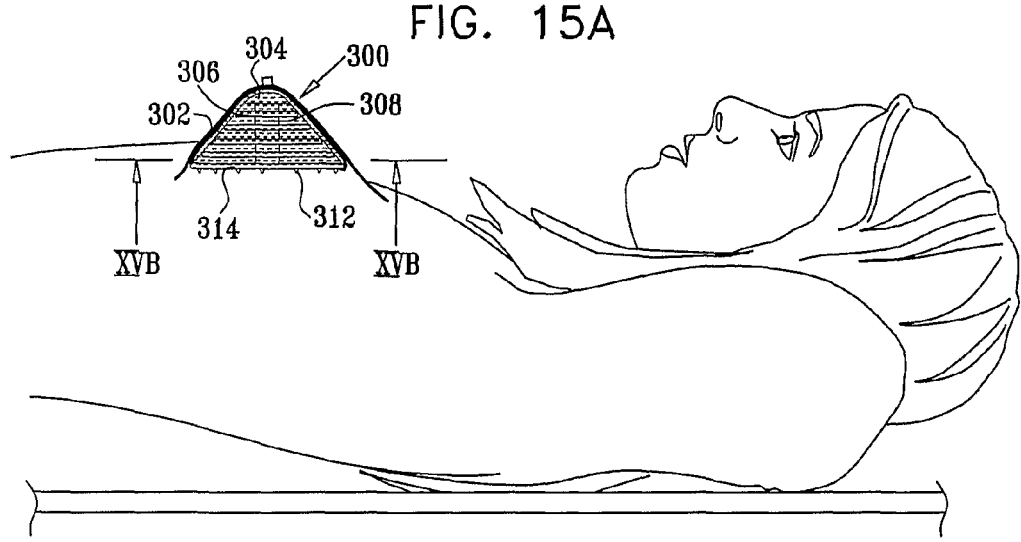
FIGS. 15A and 15B are simplified respective pictorial and sectional illustrations of the implantable breast tissue expander of FIGS. 13A and 13B, implanted in a patient positioned in a prone orientation.
Figure 15B:
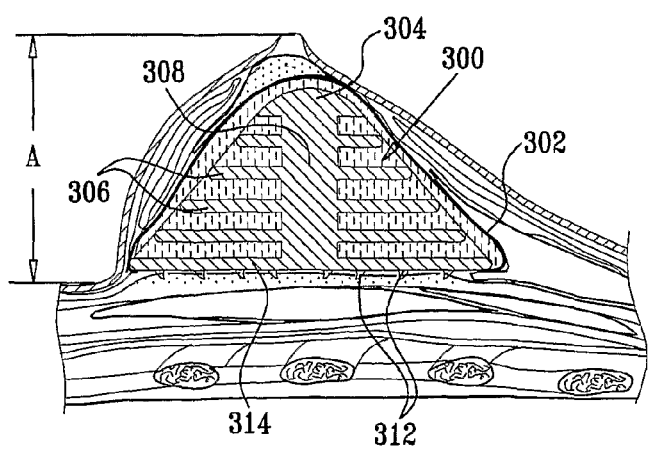

Turning to FIGS. 14A and 14B, which illustrate the tissue expander in the form of skeleton element 300 implanted in a breast, it is seen that the general three-dimensional configuration of the skeleton element 300, as it appears in FIGS. 13A and 13B, is maintained when the skeleton element 300 is implanted. Considering also FIGS. 15A and 15B, it is appreciated that the general three-dimensional configuration of the skeleton element 300, as it appears in FIGS. 13A and 13B, is maintained essentially unchanged irrespective of whether the patient is standing or lying prone, as shown by distance A in FIGS. 14B and 15B.

It is appreciated that the pressurization inside fluid enclosure 302 may be changed, as by injection of a gas or a liquid into the interior of the enclosure 302 via a suitable injection port, such as injection port 318. Alternatively, a material formed of particles, which are preferably smaller in diameter than the diameter of the injection device (not shown), may be used to change the pressurization inside enclosure 302. Such a change in pressurization may take place at any suitable time prior to or following implantation of the tissue expander.

Reference is now made to FIGS. 16A-18B, which illustrate a breast tissue expander constructed and operative in accordance with still another preferred embodiment of the present invention. The breast tissue expander of FIGS. 16A-18B is generally characterized in that it comprises a biocompatible resilient implantable structural skeleton element 350 having a predetermined overall three-dimensional shape and being operative, when implanted in human tissue, to generally maintain the predetermined three-dimensional shape generally independently of its orientation relative to gravitational acceleration.

As seen in FIGS. 16A and 16B, the skeleton element 350 is typically in the shape of a cage formed of a generally parallel array of differently sized and shaped bent elongate elements 352 which are held together by one or more transverse elongate elements, here including a surrounding elongate element 354 and two other elongate elements, designated respectively by reference numerals 356 and 358. Skeleton element 350 preferably defines at least one wall portion 360 having formed therein apertures 362, extending from an interior thereof to an exterior thereof, which are operative, when the breast tissue expander is implanted, to permit fluid flow therethrough.

It is appreciated that one or more of the various bent elongate elements 352, 354, 356 and 358 may have differing mechanical characteristics such as stiffness and resiliency. The skeleton element 350 may be integrally formed, as by injection molding. The skeleton element 350 may include variously directed positioning barbs 363 located at base locations therealong, and is preferably formed of a biocompatible plastic material, such as polyurethane or silicone.

As seen in FIG. 16C, which illustrates the breast tissue expander of FIGS. 16A and 16B rotated by approximately 45 degrees counter clockwise with respect to the orientation shown in FIG. 16A, it is a particular feature of a preferred embodiment of the present invention that skeleton element 350 is resiliently deformable from its normal shape, as shown in FIGS. 16A and 16B and designated generally in FIG. 16C by reference numeral 364, having a minimum dimension L1, to a deformed shape, designated generally by reference numeral 366, in which it has a substantially reduced minimum dimension L2, thereby to permit insertion of the skeleton element 350, in its deformed shape 366, through an aperture (not shown) in a cutaneous layer (not shown) and to allow the skeleton element 350, by virtue of its resiliency, to regain its normal shape 364 when placed at a desired location within the body (not shown).

Figure 17A:
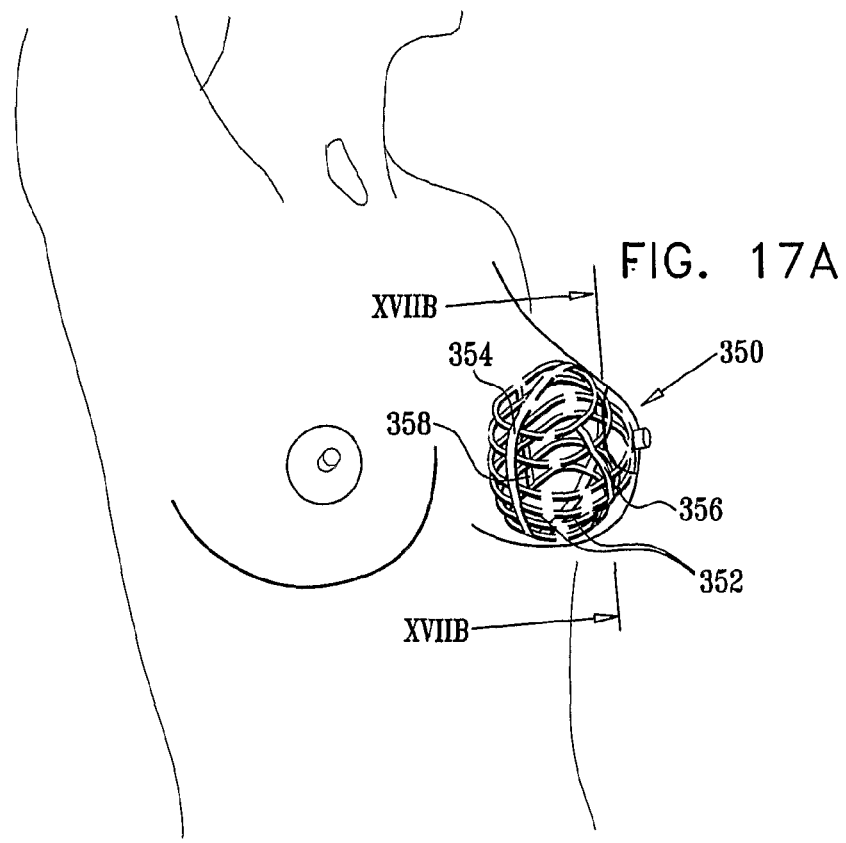
FIGS. 17A and 17B are simplified respective pictorial and sectional illustrations of the implantable breast tissue expander of FIGS. 16A and 16B, implanted in a patient positioned in a standing orientation.
Figure 17B:
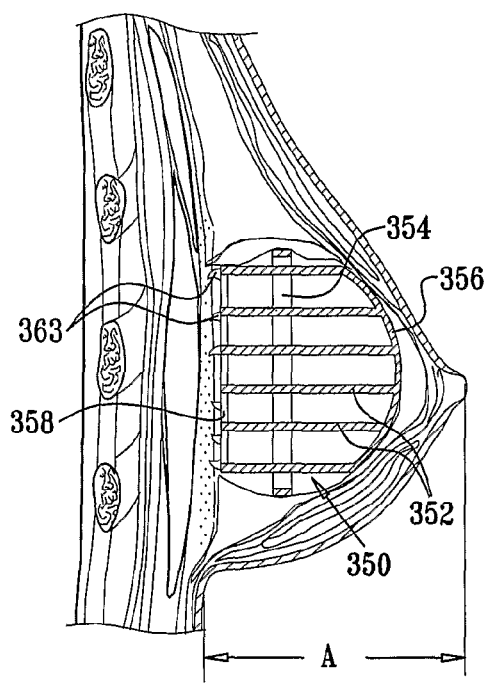
Figure 18A:
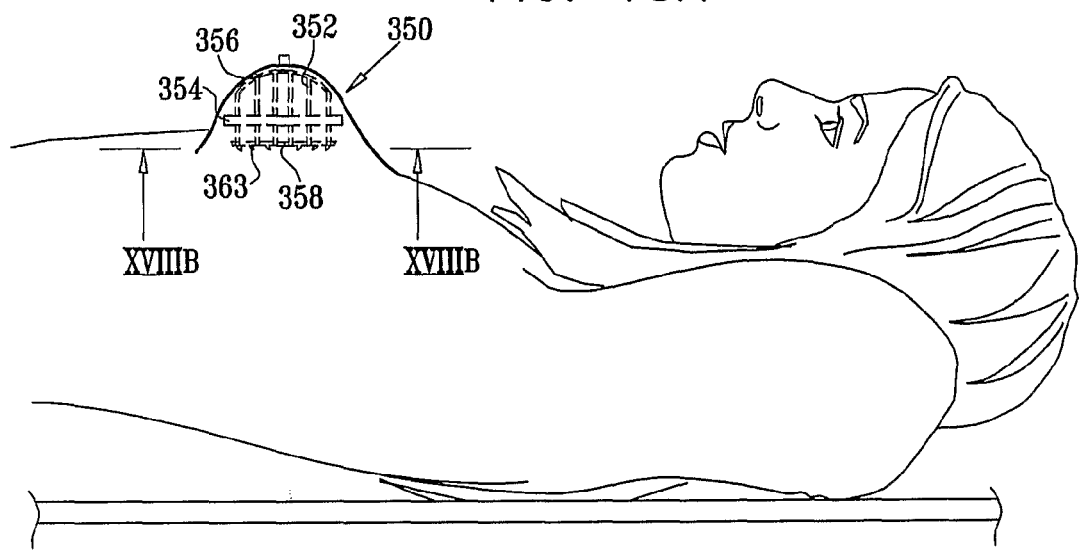
FIGS. 18A and 18B are simplified respective pictorial and sectional illustrations of the implantable breast tissue expander of FIGS. 16A and 16B, implanted in a patient positioned in a prone orientation.
Figure 18B:
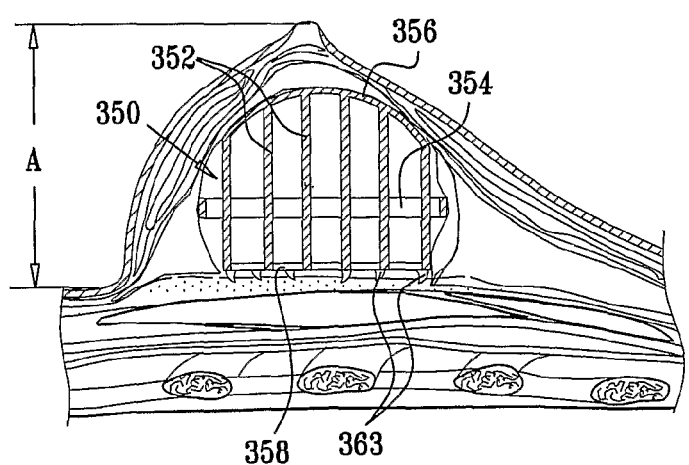

Turning to FIGS. 17A and 17B, which illustrate the tissue expander in the form of skeleton element 350 implanted in a breast, it is seen that the general three-dimensional configuration of the skeleton element 350, as it appears in FIGS. 17A and 17B, is maintained when the skeleton element 350 is implanted. Considering also FIGS. 18A and 18B, it is appreciated that the general three-dimensional configuration of the skeleton element 350, as it appears in FIGS. 18A and 18B, is maintained essentially unchanged irrespective of whether the patient is standing or lying prone, as shown by distance A in FIGS. 17B and 18B.

Reference is now made to FIGS. 19A-21B, which illustrate a breast tissue expander constructed and operative in accordance with still another preferred embodiment of the present invention. The breast tissue expander of FIGS. 19A-21B is generally characterized in that it comprises a biocompatible resilient implantable structural skeleton element 400 entirely enclosed in a fluid enclosure 402 having a shape which is generally determined by the predetermined overall three-dimensional shape of the skeleton element 400. The breast tissue expander of FIGS. 19A-21B is operative, when implanted in human tissue, to generally maintain the predetermined three-dimensional shape generally independently of its orientation relative to gravitational acceleration.

Figure 19A:
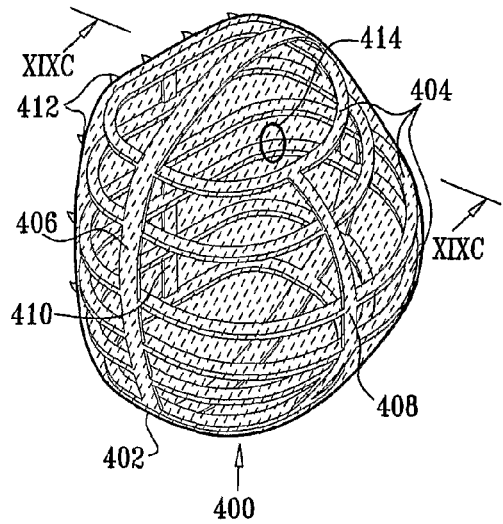
FIGS. 19A and 19B are simplified respective top and bottom pictorial view illustrations of a fluid-filled implantable breast tissue expander constructed and operative in accordance with still another preferred embodiment of the present invention.
Figure 19B:
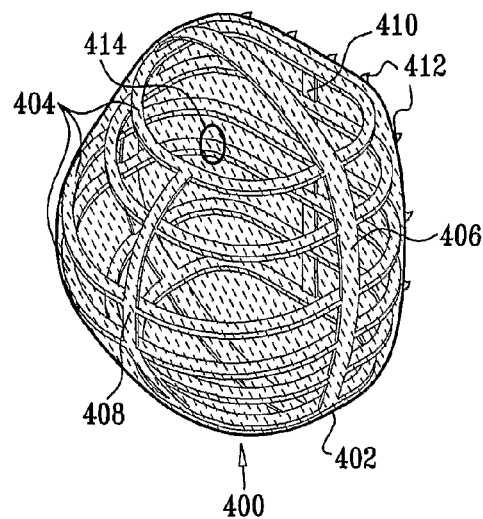

As seen in FIGS. 19A and 19B, the skeleton element 400 is typically in the shape of a cage formed of a generally parallel array of differently sized and shaped bent elongate elements 404 which are held together by one or more transverse elongate elements, here including a surrounding elongate element 406 and two other elongate elements, designated respectively by reference numerals 408 and 410. It is appreciated that one or more of the various bent elongate elements 404, 406, 408 and 410 may have differing mechanical characteristics such as stiffness and resiliency. The skeleton element 400 may be integrally formed, as by injection molding, and is preferably formed of a biocompatible plastic material, such as polyurethane or silicone.

The fluid enclosure 402 may include variously directed positioning barbs 412 located at base locations therealong. The fluid enclosure 402 is preferably formed of an elastomer, such as silicone, and preferably includes a conventional injection port 414.

Figure 19C:
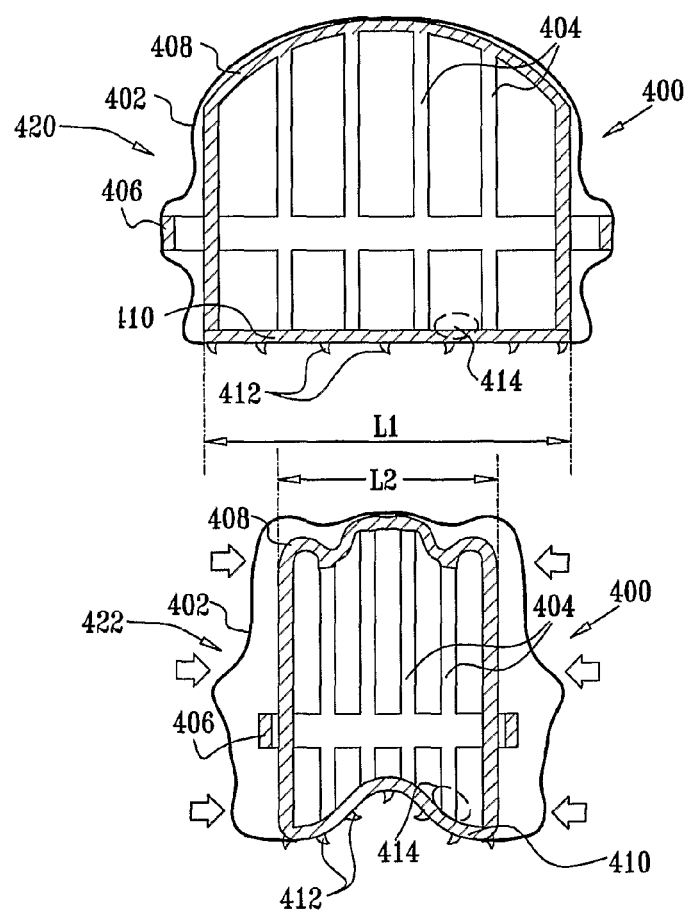
FIG. 19C is a simplified illustration showing deformation of the implantable breast tissue expander of FIGS. 19A and 19B to reduce the minimum dimension thereof.

As seen in FIG. 19C, which illustrates the breast tissue expander of FIGS. 19A and 19B rotated by approximately 45 degrees counter clockwise with respect to the orientation shown in FIG. 19A, it is a particular feature of a preferred embodiment of the present invention that skeleton element 400 and fluid enclosure 402 are resiliently deformable from their normal shape, as shown in FIGS. 19A and 19B and designated generally in FIG. 19C by reference numeral 420, having a minimum dimension L1, to a deformed shape, designated generally by reference numeral 422, in which they have a substantially reduced minimum dimension L2, thereby to permit insertion of the skeleton element 400 and the fluid enclosure 402, in their deformed shape 422, through an aperture (not shown) in a cutaneous layer (not shown) and to allow the skeleton element 400 and the fluid enclosure 402, by virtue of the resiliency of the skeleton element, to regain their normal shape 420 when placed at a desired location within the body (not shown). It is appreciated that the skeleton element 400 may be separate from the fluid enclosure 402 as illustrated in FIG. 19C. Alternatively, the skeleton element 400 may be wholly or partially joined to the fluid enclosure 402.

Figure 20A:
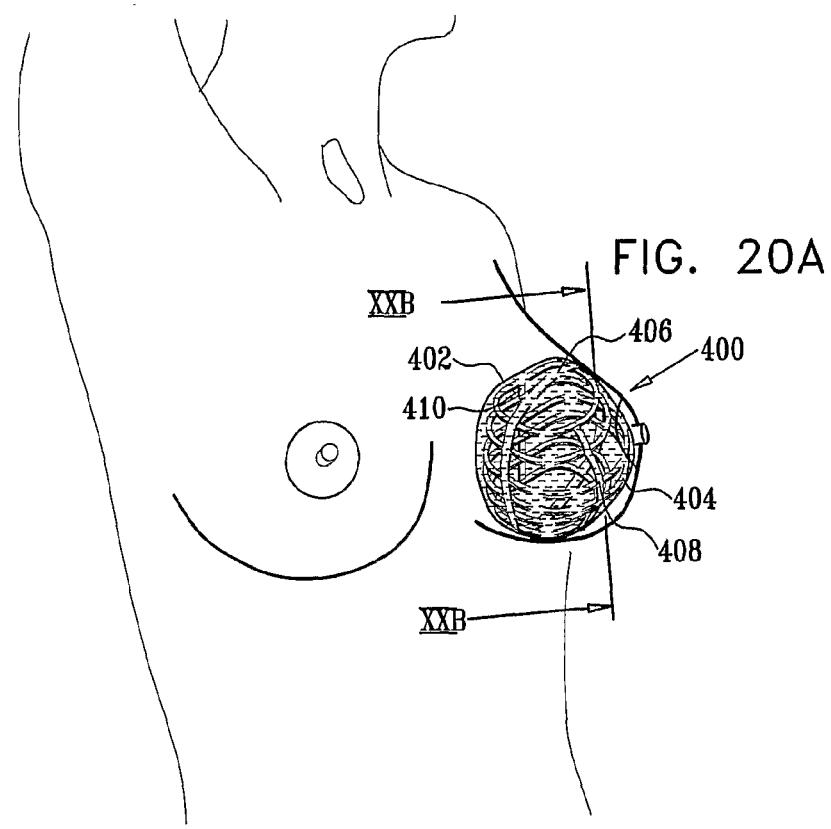
FIGS. 20A and 20B are simplified respective pictorial and sectional illustrations of the implantable breast tissue expander of FIGS. 19A and 19B, implanted in a patient positioned in a standing orientation.
Figure 20B:
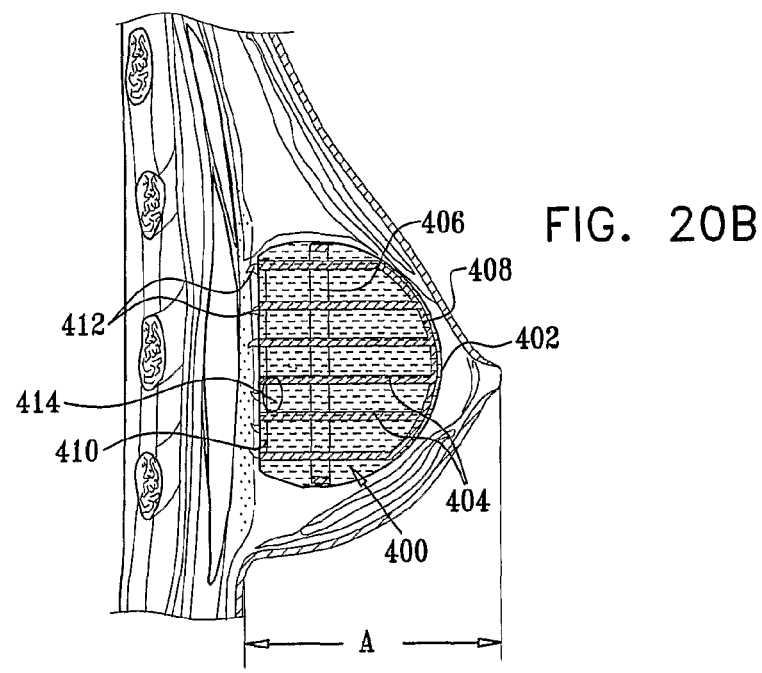
Figure 21A:
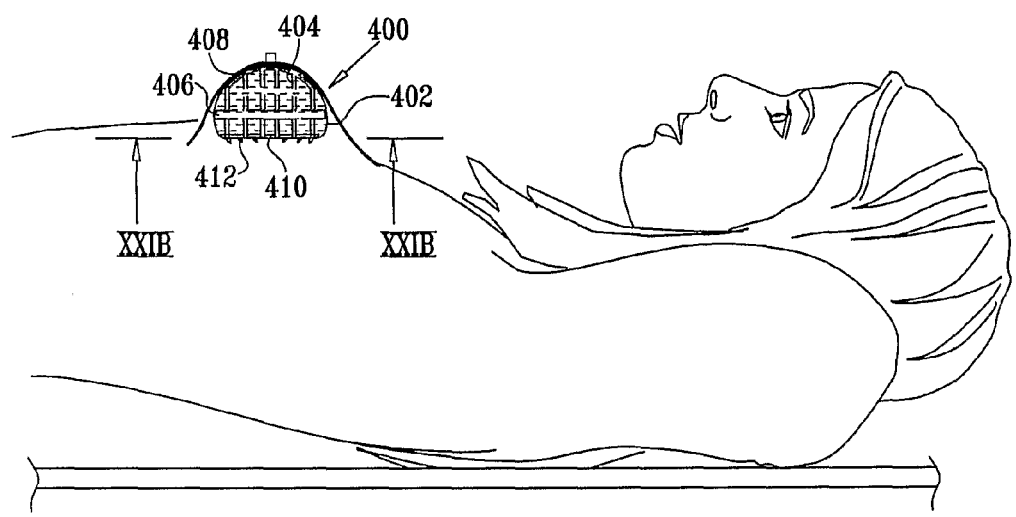
FIGS. 21A and 21B are simplified respective pictorial and sectional illustrations of the implantable breast tissue expander of FIGS. 19A and 19B, implanted in a patient positioned in a prone orientation.
Figure 21B:
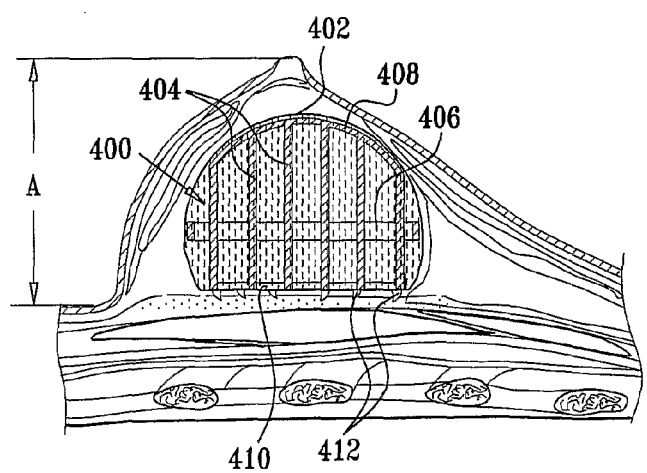

Turning to FIGS. 20A and 20B, which illustrate the tissue expander in the form of skeleton element 400 implanted in a breast, it is seen that the general three-dimensional configuration of the skeleton element 400, as it appears in FIGS. 19A and 19B, is maintained when the skeleton element 400 is implanted. Considering also FIGS. 21A and 21B, it is appreciated that the general three-dimensional configuration of the skeleton element 400, as it appears in FIGS. 19A and 19B, is maintained essentially unchanged irrespective of whether the patient is standing or lying prone, as shown by distance A in FIGS. 20B and 21B.

It is appreciated that the pressurization inside fluid enclosure 402 may be changed, as by injection of a gas or a liquid into the interior of the enclosure 402 via a suitable injection port, such as injection port 414. Alternatively, a material formed of particles, which are preferably smaller in diameter than the diameter of the injection device (not shown), may be used to change the pressurization inside enclosure 402. Such a change in pressurization may take place at any suitable time prior to or following implantation of the tissue expander.

Reference is now made to FIGS. 22A-22C, which illustrate a tissue expander constructed and operative in accordance with a further preferred embodiment of the present invention.

The tissue expander of FIGS. 22A-22C is generally characterized in that it comprises a biocompatible resilient implantable structural skeleton element 500 having associated therewith a flexible cap 502 having a shape, which is generally determined by the predetermined overall three-dimensional shape of the skeleton element 500. The tissue expander of FIGS. 22A-22C defines at least one wall portion having formed therein apertures extending from an interior thereof to an exterior thereof and is operative, when implanted in human tissue, to generally maintain the predetermined three-dimensional shape generally independently of its orientation relative to gravitational acceleration.

As seen in FIGS. 22A and 22B, the skeleton element 500 is typically in the shape of a truncated, generally conically-shaped coiled elongate element 504 and the cap 502 is preferably formed with variously directed positioning barbs 506 located on a base 508. Cap 502 and elongate element 504 are preferably formed of biocompatible plastic materials, such as polyurethane or silicone. A suitable stiffener, such as a metal wire, may be incorporated in the elongate element 504. Elongate element 504 preferably defines at least one wall portion 510 having formed therein apertures 512, extending from an interior thereof to an exterior thereof, which are operative, when the tissue expander is implanted, to permit fluid flow therethrough.

As illustrated in FIG. 22C, it is a particular feature of a preferred embodiment of the present invention that skeleton element 500 is resiliently deformable from its normal shape, as shown in FIGS. 22A and 22B and designated generally in FIG. 22C by reference numeral 514, having a minimum dimension L1, to a deformed shape, designated generally by reference numeral 516, in which it has a substantially reduced minimum dimension L2, thereby to permit insertion of the skeleton element 500, in its deformed shape 516, through an aperture (not shown) in a cutaneous layer (not shown) and to allow the skeleton element 500, by virtue of its resiliency, to regain its normal shape 514 when placed at a desired location within the body (not shown).

Figure 23A:
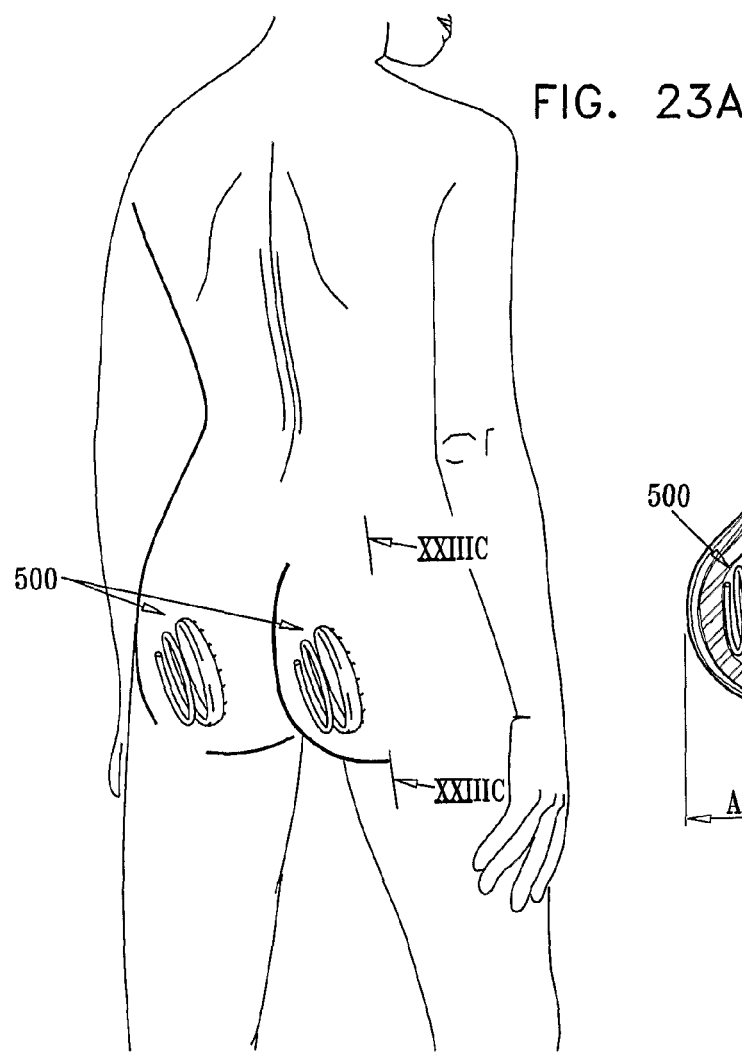
FIGS. 23A, 23B and 23C are simplified pictorial illustrations of the implantable tissue expander of FIGS. 22A and 22B implanted in the buttocks of a patient.
Figure 23B:
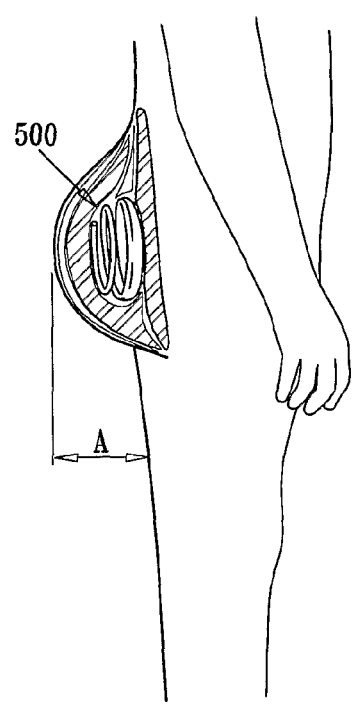
Figure 23C:
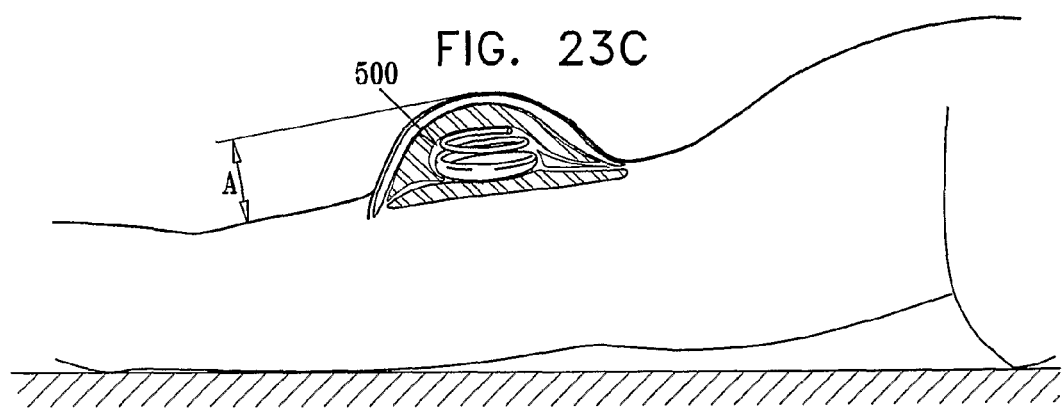

Reference is now made to FIGS. 23A, 23B and 23C, which are simplified pictorial illustrations of tissue expanders of the type shown in FIGS. 22A and 22B implanted in the buttocks of a patient.

It is seen that the general three-dimensional configuration of the skeleton element 500 is maintained when the buttocks expander is implanted, and is essentially unchanged irrespective of whether the patient is standing or lying prone, as shown by distance A in FIGS. 23B and 23C.

It is appreciated that the tissue expanders described hereinabove with reference to FIGS. 1A-23C are examples of various types of tissue expanders not limited in their application to breasts and buttocks. Similar tissue expanders may be utilized to expand any suitable human tissue.

It is appreciated that some or all of the biocompatible materials employed in the tissue expanders described hereinabove may contain medicinal materials which may be released into the surrounding tissue or into the fluid enclosure at a desired rate.

It will be appreciated by persons skilled in the art that the present invention is not limited to what has been particularly shown and described hereinabove. Rather the scope of the present invention includes both combinations and subcombinations of the various features described hereinabove as well as modifications and variations thereof as would occur to a person of skill in the art upon reading the foregoing specification and which are not in the prior art.

The invention claimed is:

1. A human implantable tissue expander comprising:
   a flexible enclosure for at least one material having at least one fluid flow characteristic; and
   a flexible and resilient structural skeleton element associated with said flexible enclosure and being operative to maintain said flexible enclosure in a predetermined three-dimensional configuration generally independently of its orientation relative to gravitational acceleration,
   wherein the overall shape of the tissue expander is determined substantially by the shape of the skeleton element and is maintained irrespectively of a filling or internal pressurization of said tissue expander.

2. A human implantable tissue expander according to claim 1 and wherein said flexible and resilient skeleton is integrally formed with said flexible enclosure.

3. A human implantable tissue expander according to claim 1 and wherein said flexible and resilient skeleton and said flexible enclosure are formed of the same material.

4. A human implantable tissue expander according to claim 1 and wherein said flexible and resilient skeleton comprises a plurality of ribs.

5. A human implantable tissue expander according to claim 1 and wherein said flexible and resilient skeleton is formed of one of polyurethane and silicone.

6. A human implantable tissue expander according to claim 1 and wherein said flexible and resilient skeleton is formed by injection molding.

7. A human implantable tissue expander according to claim 1 and wherein said flexible enclosure and said flexible and resilient skeleton are resiliently deformable to a deformed shape in which they have a substantially reduced overall minimum dimension, thereby to permit insertion of said flexible enclosure and said flexible and resilient skeleton through an aperture in a cutaneous layer when said flexible enclosure and said flexible and resilient skeleton are in said deformed shape and to allow said flexible enclosure and said flexible and resilient skeleton, by virtue of resiliency of said flexible and resilient skeleton, to regain a desired original shape when placed at a desired location within the body.

8. A human implantable tissue expander according to claim 7 and wherein said flexible enclosure does not contain said at least one material when said flexible enclosure is inserted through said aperture.

9. A human implantable tissue expander according to claim 1 and wherein said at least one material is a gas.

10. A human implantable tissue expander according to claim 1 and wherein said at least one material is a liquid.

11. A human implantable tissue expander according to claim 1 and wherein said at least one material is formed of particles.

12. A human implantable tissue expander according to claim 1 and wherein said flexible enclosure comprises an injection port.

13. A human implantable tissue expander according to claim 1 and wherein said flexible enclosure contains said at least one material.

* * * * *